US011253527B2

(12) United States Patent
Wu et al.

(10) Patent No.: US 11,253,527 B2
(45) Date of Patent: Feb. 22, 2022

(54) METHOD AND COMPOSITION FOR INHIBITING VIRUS INFECTION

(71) Applicant: ARJIL BIOTECH HOLDING COMPANY LIMITED, Hsinchu (TW)

(72) Inventors: Yeh B Wu, Hsinchu (TW); Jir-Mehng Lo, Hsinchu (TW); Hui Ju Liang, Taipei (TW); Pei-Hsin Lin, Hsinchu County (TW); Cheng Huang, Taipei (TW)

(73) Assignee: ARJIL BIOTECH HOLDING COMPANY LIMITED, Hsinchu (TW)

( * ) Notice: Subject to any disclaimer, the term of this patent is extended or adjusted under 35 U.S.C. 154(b) by 0 days.

(21) Appl. No.: 16/800,209

(22) Filed: Feb. 25, 2020

(65) Prior Publication Data

US 2020/0268771 A1  Aug. 27, 2020

Related U.S. Application Data

(60) Provisional application No. 62/809,919, filed on Feb. 25, 2019.

(51) Int. Cl.
*A61K 31/56* (2006.01)
*A61K 36/06* (2006.01)
*A61K 31/575* (2006.01)
*A61P 31/12* (2006.01)
*A61K 31/357* (2006.01)
*A61K 45/06* (2006.01)
*A61P 31/14* (2006.01)

(52) U.S. Cl.
CPC .......... *A61K 31/575* (2013.01); *A61K 31/357* (2013.01); *A61P 31/12* (2018.01); *A61K 45/06* (2013.01); *A61P 31/14* (2018.01)

(58) Field of Classification Search
CPC ........ A61K 31/575; A61K 36/07; A61P 31/12
USPC ............ 514/170, 171, 177, 178; 424/195.16
See application file for complete search history.

(56) References Cited

U.S. PATENT DOCUMENTS

| 2009/0048330 A1 | 2/2009 | Hattori et al. |
| 2013/0113297 A1* | 5/2013 | Miyamoto ............. H02J 50/40 307/104 |
| 2017/0226150 A1 | 8/2017 | Wu et al. |

FOREIGN PATENT DOCUMENTS

WO   WO 2016/161138 A1   10/2016

OTHER PUBLICATIONS

Chen et al. "Antcin A, a steroid-like compound from Antrodia camphorate, exert anti-inflammatory effect via mimicking glucocorticoids," Acta Pharmacologica Sinica, 2011, vol. 32, pp. 904-911, (Year: 2011).*

(Continued)

*Primary Examiner* — Shengjun Wang
(74) *Attorney, Agent, or Firm* — Birch, Stewart, Kolasch & Birch, LLP

(57) ABSTRACT

The present invention pertains to a composition for preparing a medicament for preventing and/or treating a virus infection, especially a hepatitis B virus infection and/or a herpes simplex virus, and uses thereof.

6 Claims, 15 Drawing Sheets

(56) References Cited

OTHER PUBLICATIONS

He et al. "Anti-herpes simplex virus activities of bioactive extract from Antrodia camphorata mycelia," Antiviral Therapy, 2016, vol. 21, pp. 377-383 (Year: 2016).*

Tsai et al., "Antrodia cinnamomea Induces Autophagic Cell Death via the CHOP/TRB3/Akt/mTOR Pathway in Colorectal Cancer Cells," Scientific Reports, vol. 8, Article No. 17424, 2018 (Published online Nov. 27, 2018), pp. 1-12.

Written Opinion of the International Searching Authority and International Search Report, dated Jun. 11, 2020, for International Application No. PCT/US2020/019583.

\* cited by examiner

METHOD AND COMPOSITION FOR INHIBITING VIRUS INFECTION

CROSS REFERENCE TO RELATED APPLICATIONS

This application claims the benefit of and priority to U.S. Provisional Application Ser. No. 62/809,919, filed Feb. 25, 2019, which is incorporated herein by reference in its entirety.

FIELD OF THE INVENTION

The present invention provides a method and composition of inhibiting virus infections.

BACKGROUND OF THE INVENTION

Viruses, made of genetic material inside of a protein coating, invade living, normal cells and use those cells to multiply and produce other viruses like themselves, that may cause familiar infectious disease such as flu and warts, or may cause severe illness such as smallpox and acquired immune deficiency syndrome (AIDS).

For example, there are 5 different types of hepatitis viruses i.e., A, B, C, D and E along with X and G. Hepatitis A and E viruses are induced by consumption of pestiferous water and food. However, hepatitis B, C, and D viruses are caused by parenteral, adjoin with infected bodily fluids. In addition, hepatitis C and D virus infections are also on the increase and effective treatments are needed.

Hepatitis B virus (HBV) causes acute and chronic viral hepatitis in humans. HBV infection is often associated with severe liver diseases, including cirrhosis and hepatocellular carcinoma (HCC) [1]. The prevalence of HBV infection in the world is very high. About 350 million individuals are chronically infected, despite the availability of an effective vaccine for more than 25 years. Approximately an 100-fold increase in the relative risk of HCC among HBV carriers compared to non-carriers [2].

An increasing number of patients with HBV infection cannot use the currently approved anti-HBV drugs, including interferon alpha or nucleos(t)ide analogues that inhibit the viral reverse transcriptase, due to the adverse effects and the emergence of drug resistance [3].

Therefore, the search for effective and safe as well as affordable anti-HBV agents aiming at the interference with other steps in the viral life cycle is required to improve the treatment outcome.

HBV is a small DNA virus consisting of a nucleocapsid which protects the 3.2 kb viral genome [4]. The HBV nucleocapsid is surrounded by an envelope, consists of hepatitis B surface antigens (HBsAgs). HBsAgs are encoded in one open reading frame with three in-phase start codons. The MHBsAg has a 55-amino-acid (aa) extension from the S domain that is known as the pre-S2 domain. The LHBsAg has a further 108-aa region that extends from the pre-S2 domain to compose the pre-S1 domain. Recently, sodium taurocholate cotransporting polypeptide (NTCP) was identified as an HBV receptor [5, 6]. Entry of HBV into uninfected hepatocytes has long been proposed as a potential target for antiviral intervention [7]. On the other hand, HepG2.2.15 cells encompass HBV whole genome, which was widely used to study HBV replication, assembly, and secretion.

The attachment to hepatocyte by HBV during infection has long been proposed to be a potential target for antiviral intervention. It is thought that molecules specifically binding to HBV particles may interfere with viral attachment and hence reduce or block subsequent infection [8].

Insights into the early infection events of human HBV are limited because of the lack of a cell culture system supporting the full replication cycle. To date, two cell types have been shown to be susceptible to HBV infection. One is the human hepatoma cell line HepaRG, which becomes infectable after dimethyl sulfoxide (DMSO)-induced differentiation [7, 9], while the other cell type, normal human primary hepatocytes, is readily infected by HBV [10, 11], but the limited lifetime of the cells in vitro and the lack of a consistent source severely restrict its further application.

Besides, Herpes simplex virus (HSV) also consists of a DNA genome encased within a protein coating. Herpes simplex virus types 1 and 2 (HSV-1 and HSV-2) are the causative agents of human diseases, including gingivostomatitis, pharyngitis, herpes labialis, encephalitis, eye and genital infection [12]. Herpesvirus infections generally involve a mild or asymptomatic primary phase followed by persistence of the virus in a non-replicating latent state or at a clinically undetectable level of replication [13]. Primary infection with HSV-1 most commonly involves the mouth and/or throat resulting in gingivostomatitis and pharyngitis. Following recovery from the primary oropharyngeal infection, the individual retains HSV DNA in the trigeminal ganglion for life and may suffer recurrent attacks of herpes labialis. Studies have also revealed a possible association between some members of the herpesvirus family and periodontal diseases [14]. Human herpesviruses may occur in periodontitis lesions with relatively high prevalence [15]. HSV is related to the severity of periodontal diseases in terms of clinical attachment loss [16]. Viral gingival infections may act to impair host defense mechanisms and thereby set the stage for overgrowth of pathogenic oral bacteria [15, 17].

HSV commonly attacks mucosa, skin, eyes and the nervous system and is capable of infecting a wide variety of cells [18]. Human gingival mucosa organ culture can be infected with HSV-1 and HSV-2 [19]. In addition, human gingival keratinocytes and gingival fibroblasts which are grown in vitro support the multiplication of HSV [20, 21]. HSV-1 encodes viral thymidine kinase, which indirectly metabolizes acyclovir into acyclovir triphosphate, a chain terminator substrate for HSV DNA polymerase and stops viral DNA replication [22]. However, resistance of HSV to acyclovir has been reported in 5-30% of cases [23]). Acyclovir-resistant HSV-1 strains occur frequently in immunocompromised patients, which may result in severe complications [24]. Due to the lack of vaccine, topical microbicides may be an important strategy for preventing HSV transmission.

Still, it is desirable to develop a new antiviral therapy or medicament.

BRIEF SUMMARY OF THE INVENTION

It is unexpectedly found in the present invention that the preparations of *Antrodia camphorata*, and active ingredients of *Antrodia camphorata* are effective in inhibition of virus infections, especially a Hepatitis B virus (HBV) infection and/or a Herpes simplex virus (HSV) infection.

It was ascertained in the examples that the preparation of *Antrodia camphorata* was able to inhibit a virus replication, an assembly or a release of viral particles; and an entry of virus.

It is an object of the present invention to provide a method for preventing and/or treating a virus infection, comprising administering to a subject in need thereof a preparation of *Antrodia camphorate* and/or active ingredients of *Antrodia camphorata*.

In one example, the virus infection to be prevented and/or treated in the present invention is selected from the group consisting of a hepatitis virus infection, an influenza virus infection, a herpes simplex virus infection, an enterovirus infection, a rotavirus infection, a dengue virus infection, a poxvirus infection, a human immunodeficiency virus infection, an adenovirus infection, a coronavirus infection, an arenavirus infection, a measles virus infection, a retrovirus infection and a Norovirus infection.

In one example, the present invention to provide a method for preventing and/or treating an HBV infection, comprising administering to a subject in need thereof a preparation of *Antrodia camphorata*.

In another example, the present invention to provide a method for preventing and/or treating an HSV infection, comprising administering to a subject in need thereof a preparation of *Antrodia camphorata*.

Actually, it would be derived from the findings that the inhibition of hepatitis virus infection by inhibiting the virus replication, the assembly, the release of viral particles, and the entry of virus to develop a broad-spectrum antiviral agents because they inhibit the development of viruses.

In another object, the present invention provides a pharmaceutical composition for preventing and/or treating a virus infection, which comprises a therapeutically effective amount of a preparation of *Antrodia camphorate* and/or active ingredients of *Antrodia camphorata*, and a pharmaceutically acceptable carrier.

In one embodiment of the invention, the preparation of *Antrodia camphorate* includes but not is limited to an extract of *Antrodia camphorate*, an extract of a dish culture of *Antrodia camphorate*, an extract of *Antrodia camphorata* fruit body, and active compounds isolated from the above-mentioned extracts.

In one example of the invention, the active compound may be one or more selected from the group consisting of:

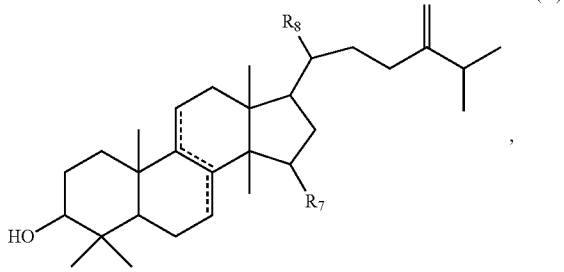
(Ia)

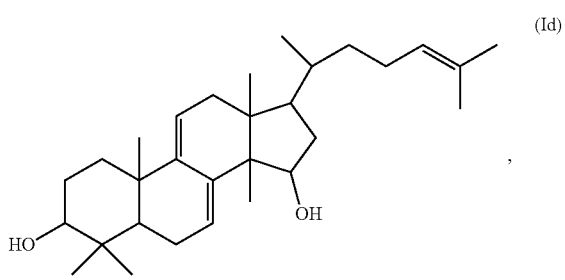
(Ib)

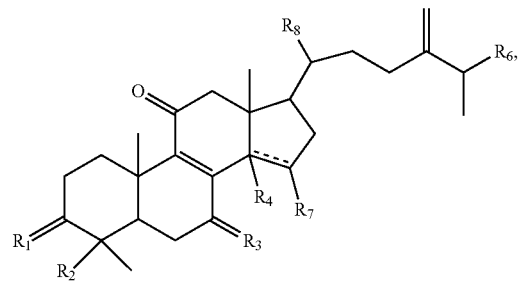
(Ic)

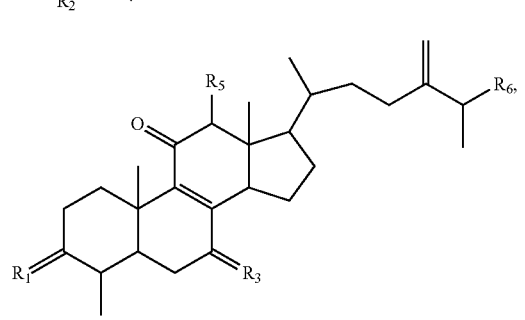
(Id)

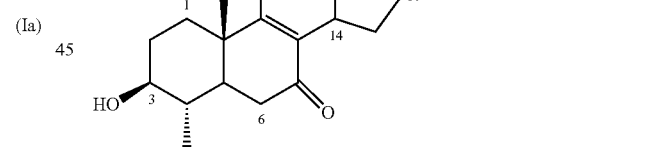
(Ie)

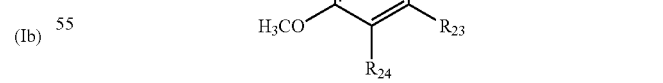
(II)

wherein $R_1$ is O, α-OH or β-H; $R_2$ is H or OH; $R_3$ is O, α-H, β-OAc or $H_2$; $R_4$ is H or OH; $R_5$ is H, or OH; $R_6$ is COOH or COO($CH_2$)n-$CH_3$; n is an integer from 0-3; $R_7$ is H, OH or OAc; $R_8$ is $CH_3$ or COOH; $R_{21}$ is $CH_3$, COOH, or COO($CH_2$)n-$CH_3$; n is an integer from 0-3; each of $R_{22}$, $R_{23}$, $R_{24}$ is $OCH_3$, or $R_{22}$ and $R_{23}$ together form a O—$CH_2$—O; or $R_{23}$ and $R_{24}$ together form a O—$CH_2$—O; the dotted line represents a single bond or a double bond.

In one particular example of the present invention, the compound is dehydroeburicoic acid:

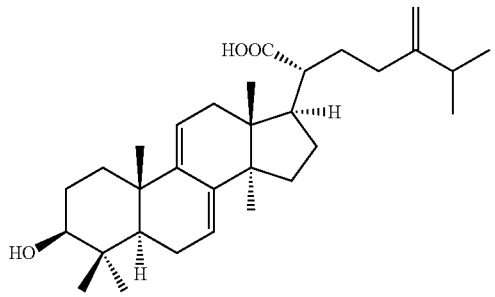

In another example of the present invention, the compound is versisponic acid D:

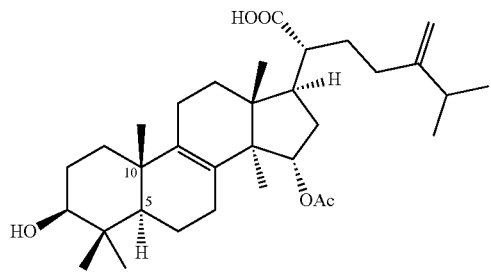

In another example of the present invention, the compound is dehydrosulphurenic acid (dehydrosulfurenic acid)

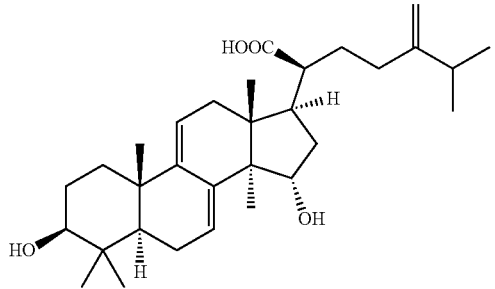 [SMILES: C=C(CC[C@H](C(=O)O)[C@H]1C[C@H](O)[C@@]2(C)C3=CC[C@H]4C(C)(C)[C@@H](O)CC[C@]4(C)C3=CC[C@]12C)C(C)C]

In one particular example of the present invention, the compound of formula (II) is 4,7-Dimethoxy-5-methyl-1,3-benzodioxole:

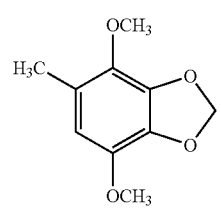

In one example of the present invention, the compound is antcin A:

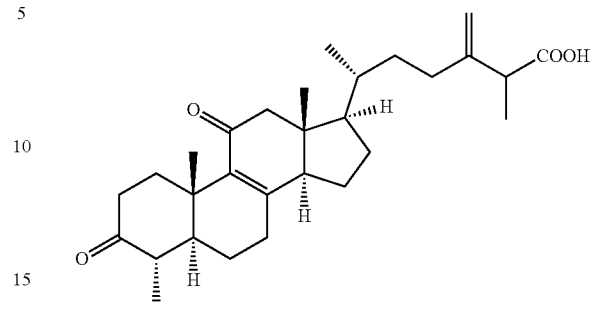

In one example of the present invention, the compound is antcin B:

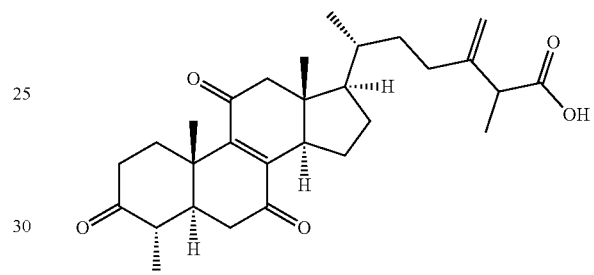

In one example of the present invention, the compound is antcin C:

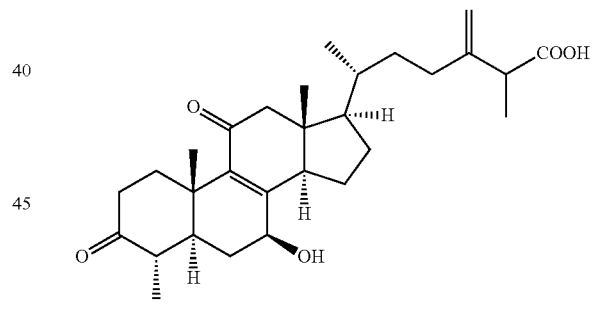

In one example of the present invention, the compound is antcin H:

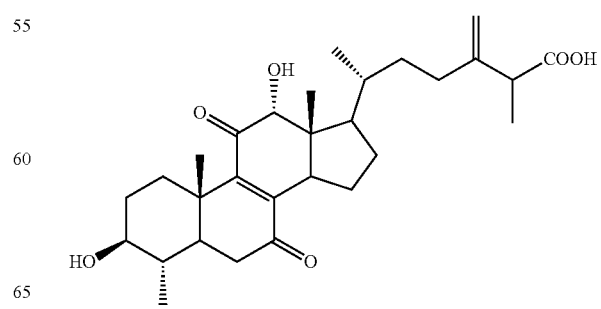

In one example of the present invention, the compound is antcin K:

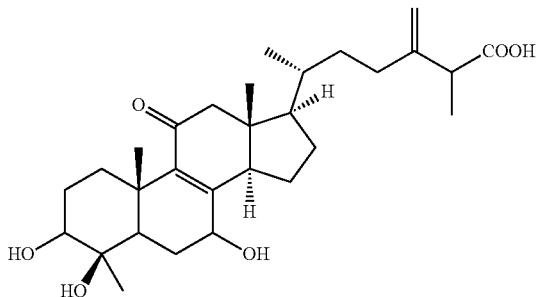 [SMILES: C=C(CC[C@@H](C)[C@H]1CC[C@H]2C3=C(C(=O)C[C@]12C)[C@@]1(C)CCC(O)[C@](C)(O)C1CC3O)C(C)C(=O)O]

In one further aspect, the present invention provides a method for treating a virus infection comprising administering to a subject in need thereof a therapeutically effective amount of a composition/pharmaceutical composition disclosed herein, and at least one additional anti-viral therapeutic agent.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1A:
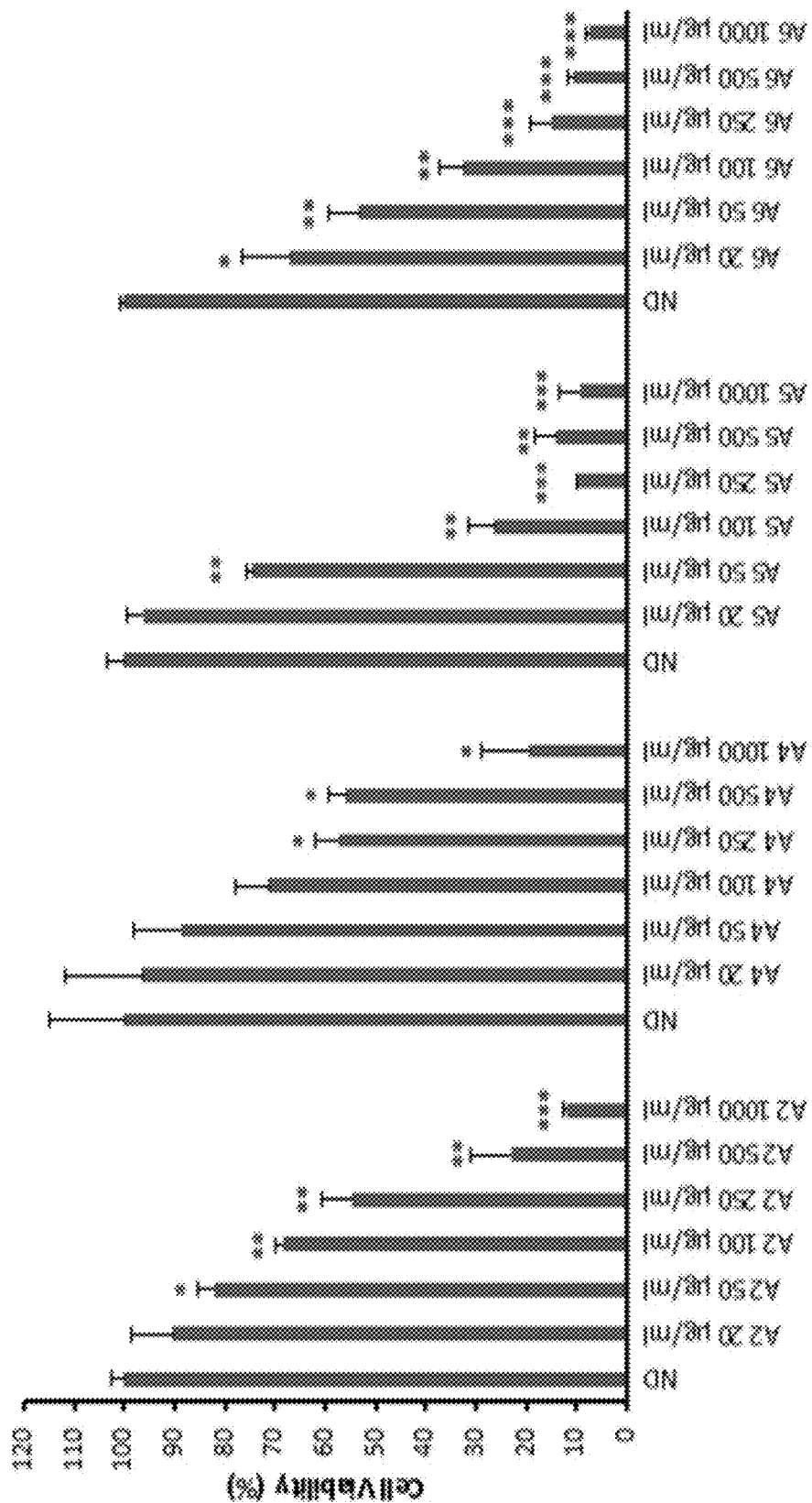
FIG. 1A shows an effect of *Antrodia camphorata* fruit body extracts on cell viability. HepG2.2.15 cells were treated with 0-1000 μg/ml *Antrodia camphorata* fruit body extracts for 48 h, then the MTT assay was performed to detect cell viability. *, P<0.05; , P<0.01; *, P<0.001.

The above summary of the present invention will be further described with reference to the embodiments of the following examples. However, it should not be understood that the content of the present invention is only limited to the following embodiments, and all the inventions based on the above-mentioned contents of the present invention belong to the scope of the present invention.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The present invention provides a method for preventing and/or treating a virus infection, comprising administering to a subject in need thereof a preparation of *Antrodia camphorate* and/or active ingredients of *Antrodia camphorata*.

The present invention also provides a composition/pharmaceutical composition for preventing and/or treating a virus infection, especially a Hepatitis B virus (HBV) infection and/or a Herpes simplex virus (HSV) infection, which comprises a therapeutically effective amount of a preparation of *Antrodia camphorate* and/or active ingredients of *Antrodia camphorata*, and a pharmaceutically acceptable carrier.

According to the invention, the preparation of *Antrodia camphorate* includes but not is limited to an extract of *Antrodia camphorate*, an extract of a dish culture of *Antrodia camphorate*, an extract of *Antrodia camphorata* fruit body, and active compounds isolated from the above-mentioned extracts, and the derivatives thereof.

More particularly, the active compounds isolated from *Antrodia camphorata* are one or more selected from the group consisting of the following:

(1)

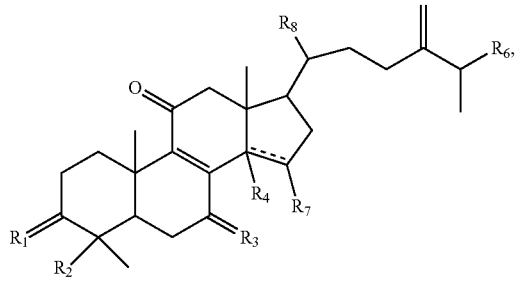
(Ia)

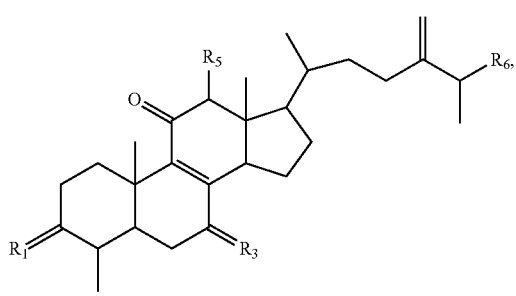
(Ib)

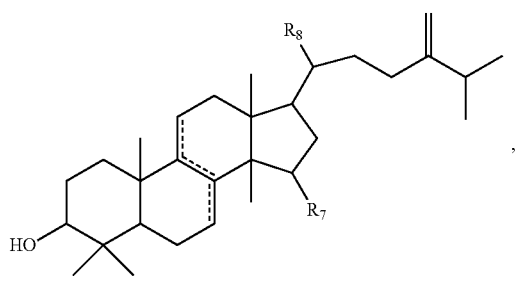
(Ic)

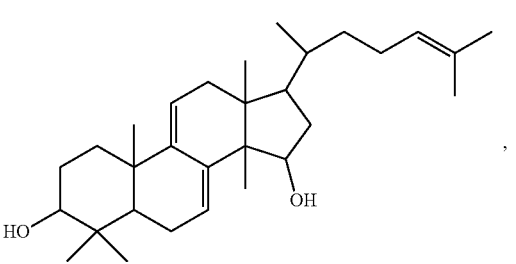
(Id)

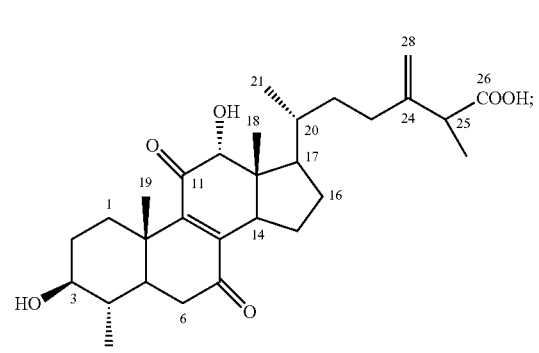
(Ie)

wherein $R_1$ is O, α-OH or β-H; $R_2$ is H or OH; $R_3$ is O, α-H, β-OAc or $H_2$; $R_4$ is H or OH; $R_5$ is H or OH; $R_6$ is COOH or $COO(CH_2)n\text{-}CH_3$; $R_7$ is H, OH, or OAc; $R_8$ is $CH_3$ or COOH; the dotted line represents a single bond or a double bond; n is an integer from 0-3; or (2)

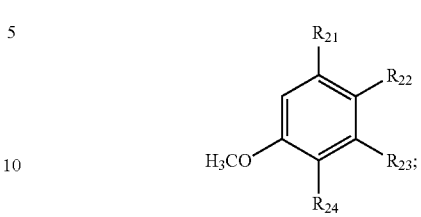
(II)

wherein $R_{21}$ is $CH_3$ or COOH, or $COO(CH_2)n\text{-}CH_3$; n is an integer from 0-3; each of $R_{22}$, $R_{23}$, $R_{24}$ is $OCH_3$, or $R_{22}$ and $R_{23}$ together form a O—$CH_2$—O; or $R_{23}$ and $R_{24}$ together form a O—$CH_2$—O.

In the example of the invention, the compound may be:

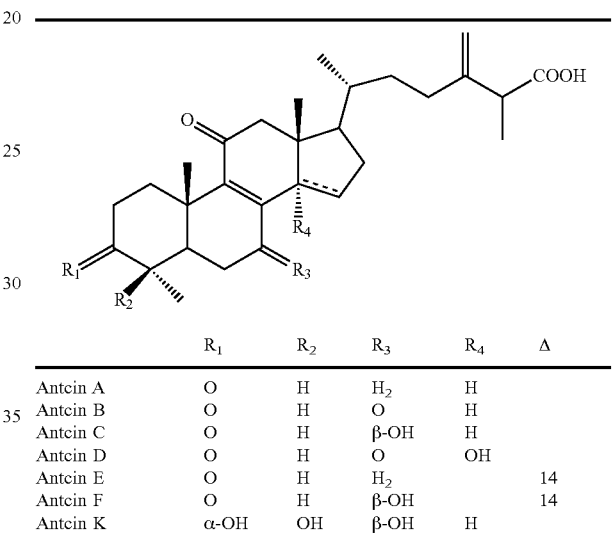

| | $R_1$ | $R_2$ | $R_3$ | $R_4$ | Δ |
|---|---|---|---|---|---|
| Antcin A | O | H | $H_2$ | H | |
| Antcin B | O | H | O | H | |
| Antcin C | O | H | β-OH | H | |
| Antcin D | O | H | O | OH | |
| Antcin E | O | H | $H_2$ | | 14 |
| Antcin F | O | H | β-OH | | 14 |
| Antcin K | α-OH | OH | β-OH | H | |

In another example of the invention, the compound may be:

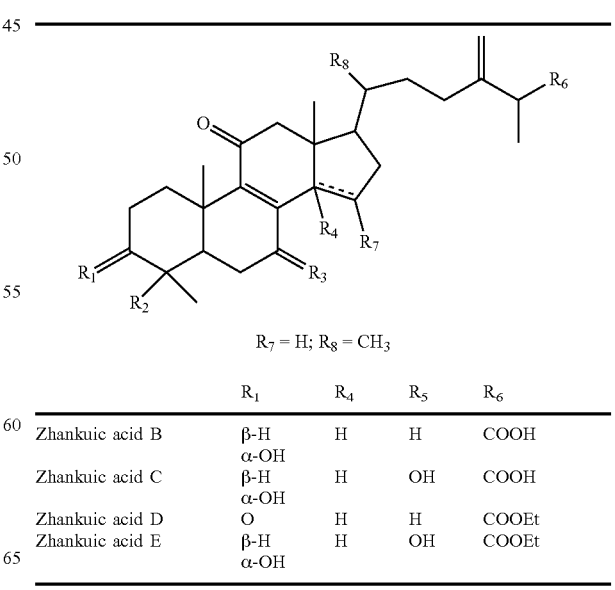

$R_7$ = H; $R_8$ = $CH_3$

| | $R_1$ | $R_4$ | $R_5$ | $R_6$ |
|---|---|---|---|---|
| Zhankuic acid B | β-H α-OH | H | H | COOH |
| Zhankuic acid C | β-H α-OH | H | OH | COOH |
| Zhankuic acid D | O | H | H | COOEt |
| Zhankuic acid E | β-H α-OH | H | OH | COOEt |

In one yet example of the invention, the compound may be:

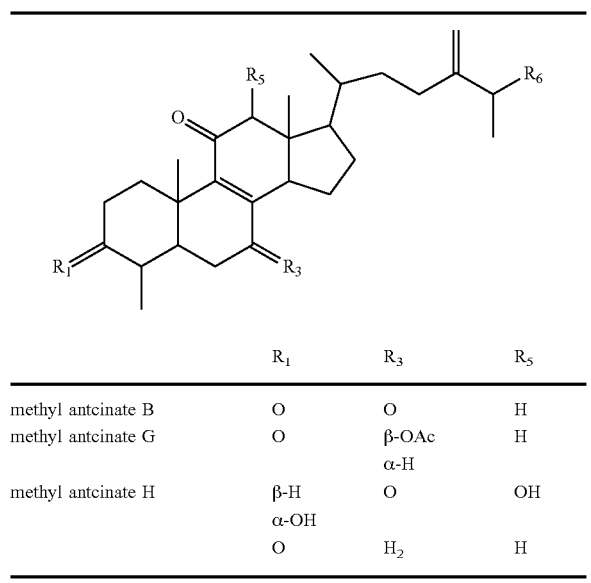

| | $R_1$ | $R_3$ | $R_5$ |
|---|---|---|---|
| methyl antcinate B | O | O | H |
| methyl antcinate G | O | β-OAc<br>α-H | H |
| methyl antcinate H | β-H<br>α-OH | O | OH |
| | O | $H_2$ | H |

In further example of the invention, the compound may be:

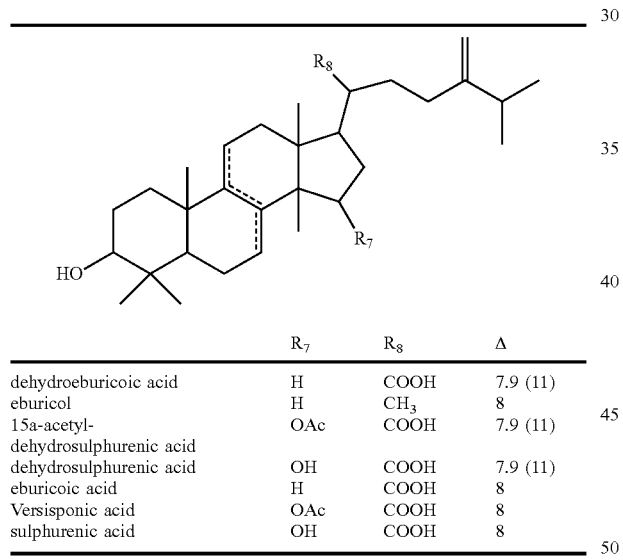

| | $R_7$ | $R_8$ | Δ |
|---|---|---|---|
| dehydroeburicoic acid | H | COOH | 7.9 (11) |
| eburicol | H | $CH_3$ | 8 |
| 15a-acetyl-dehydrosulphurenic acid | OAc | COOH | 7.9 (11) |
| dehydrosulphurenic acid | OH | COOH | 7.9 (11) |
| eburicoic acid | H | COOH | 8 |
| Versisponic acid | OAc | COOH | 8 |
| sulphurenic acid | OH | COOH | 8 |

In one particular example of the invention, the compound may be lanostane:

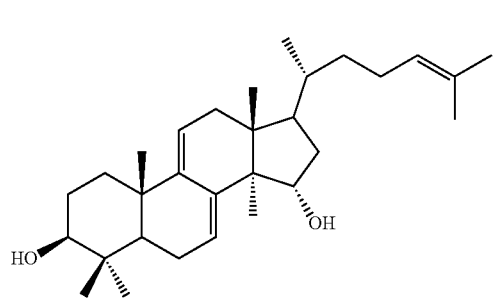

In addition, the compound of formula (II) may be

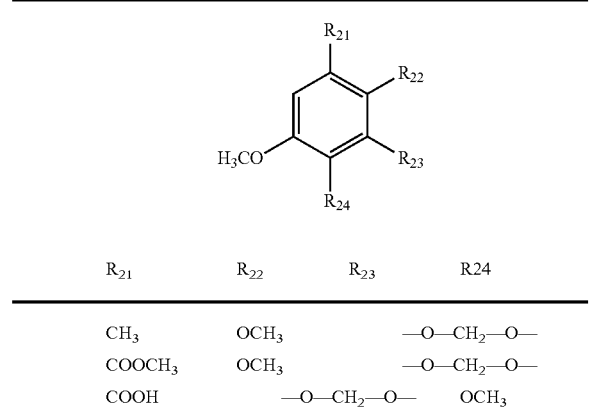

| $R_{21}$ | $R_{22}$ | $R_{23}$ | $R24$ |
|---|---|---|---|
| $CH_3$ | $OCH_3$ | | —O—$CH_2$—O— |
| $COOCH_3$ | $OCH_3$ | | —O—$CH_2$—O— |
| COOH | | —O—$CH_2$—O— | $OCH_3$ |

Accordingly, the compound is selected from the group consisting of:

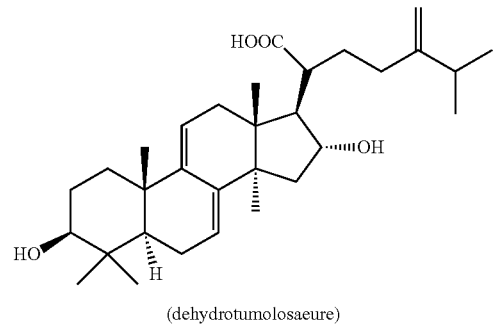

(dehydrotumolosaeure)

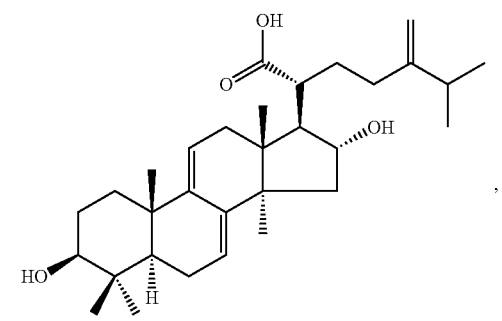

(dehydrotumulosic acid)

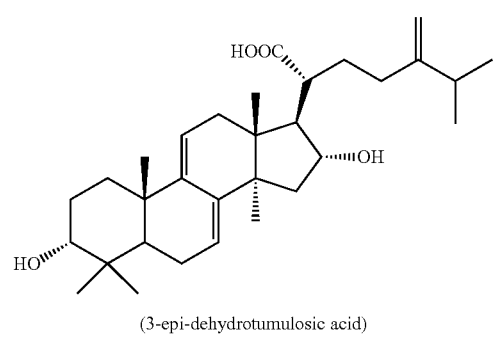

(3-epi-dehydrotumulosic acid)

-continued

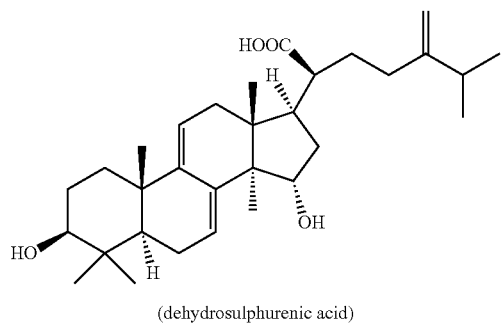
(dehydrosulphurenic acid)

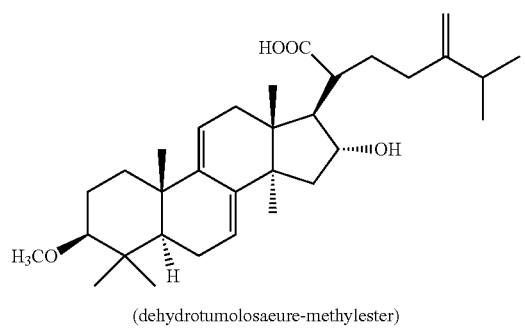
(dehydrotumolosaeure-methylester)

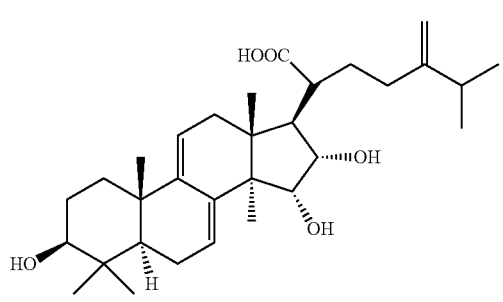
((20ξ)-3β,15α,16α-trihydroxy-24-methyllanosta-7,9(11),24(241)-trien-21-oic acid; 15α-hydroxydehydrotumulosic acid)

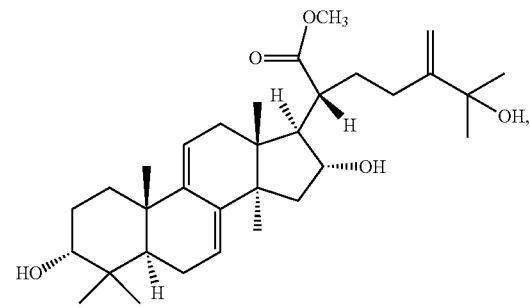
(methyl 25-hydroxy-3-epidehydrotumulosate(methyl))

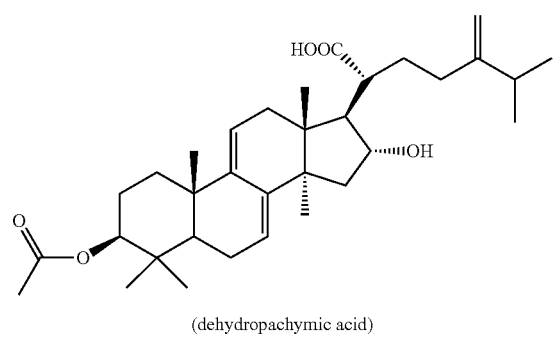
(dehydropachymic acid)

-continued

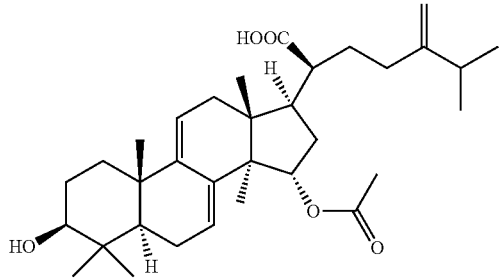
(15α-acetyldehydrosulfurenic acid)

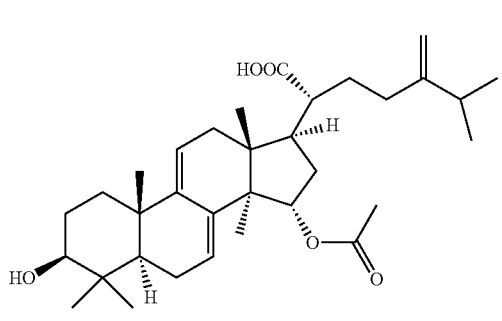
(15α-acetyldehydrosulphurenic acid)

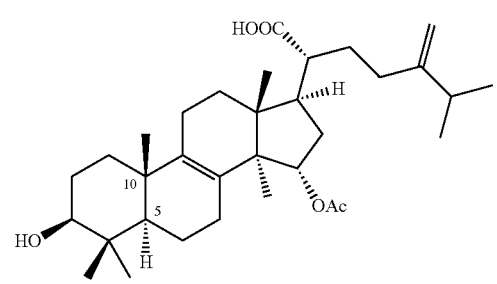
(versisponic acid D)

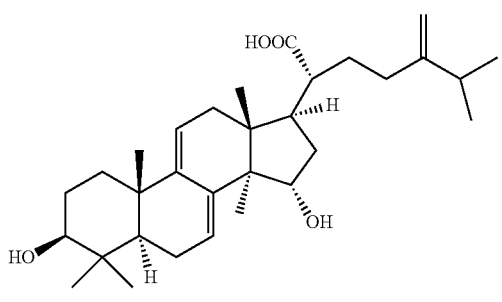
(dehydrosulphurenic acid)

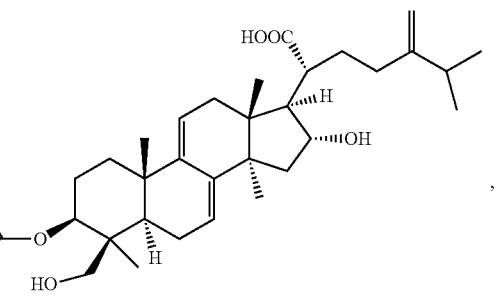
, and (29-hydroxydehydropachymic acid; (3β,16α)-3-(acetyloxy)-16,29-dihydroxy-24-methylidenelanosta-7,9(11)-dien-21-oic acid)

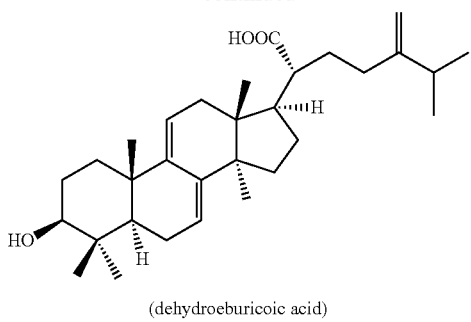

(dehydroeburicoic acid)

According to the invention, the compound is selected from the group consisting of

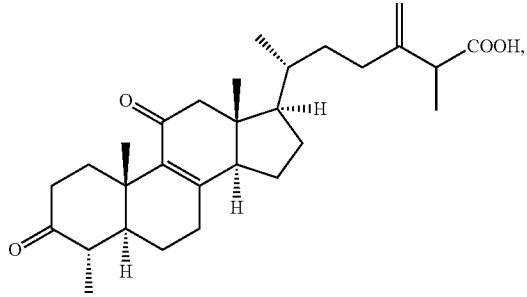

(antcin A)

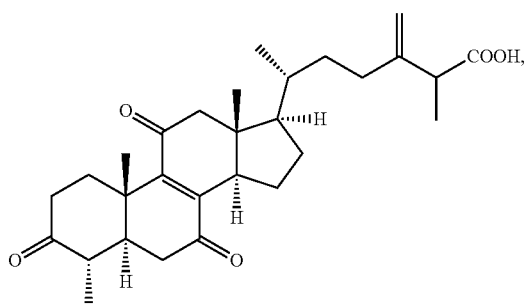

(antcin B)

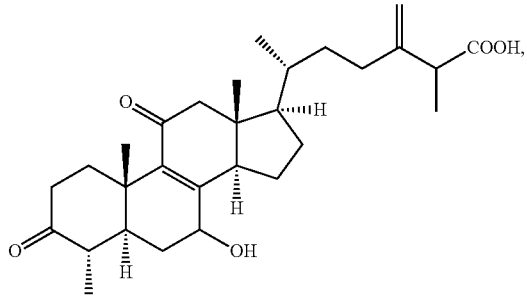

(antcin C)

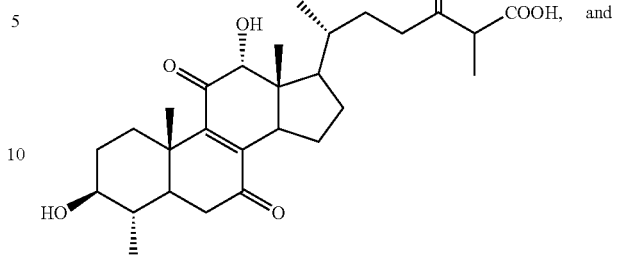

(antcin H)

(antcin K)

In one particular example of the invention, the compound of formula (II) is

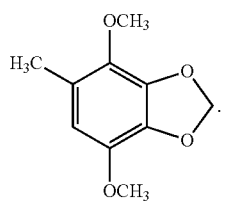

(4,7-dimethoxy-5-methyl-1,3-benzodioxole)

The term "virus" as used herein refers to any virus, which is a small infectious agent that replicates only inside the living cells of an organism, which can infect all types of life forms, from animals and plants to microorganisms, including bacterials and archaea. Exemplified viruses include, without limitation, a hepatitis virus, an influenza virus, a herpes simplex virus, an enterovirus, a rotavirus, a dengue virus, a poxvirus, a human immunodeficiency virus, an adenovirus, a measles virus, a retrovirus or a Norovirus.

The term "treating" as used herein refers to the application or administration of a composition including one or more active agents to a subject afflicted with a disease, a symptom or conditions of the disease, or a progression of the disease, with the purpose to cure, heal, alleviate, relieve, alter, remedy, ameliorate, improve, or affect the disease, the symptoms or conditions of the disease, the disabilities induced by the disease, or the progression of the disease.

The term "subject" as used herein includes human or non-human animals, such as companion animals (e.g. dogs, cats, etc.), farm animals (e.g. cattle, sheep, pigs, horses, etc.), or experimental animals (e.g. rats, mice, guinea pigs, etc.).

The term "therapeutically effective amount" as used herein refers to an amount of a pharmaceutical agent which, as compared to a corresponding subject who has not received such amount, results in an effect in treatment, healing, prevention, or amelioration of a disease, disorder, or side effect, or a decrease in the rate of advancement of a disease or disorder. The term also includes within its scope amounts effective to enhance normal physiological function.

For use in therapy, the therapeutically effective amount of the compound is formulated as a pharmaceutical composition for administration. Accordingly, the invention further provides a pharmaceutical composition comprising a therapeutically effective amount of the preparation of *Antrodia camphorata* or the active compounds isolated from *Antrodia camphorata*, and one or more pharmaceutically acceptable carriers.

For the purpose of delivery and absorption, a therapeutically effective amount of the active ingredient according to the present invention may be formulated into a pharmaceutical composition in a suitable form with a pharmaceutically acceptable carrier. Based on the routes of administration, the pharmaceutical composition of the present invention comprises preferably from 0.1% to 100% in weight of the total weight of the active ingredient.

The term "pharmaceutically acceptable carrier" used herein refers to a carrier(s), diluent(s) or excipient(s) that is acceptable, in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation. According to the invention, the pharmaceutical composition may be adapted for administration by any appropriate route, including but not limited to oral, rectal, nasal, topical, vaginal, or parenteral route. In one particular example of the invention, the pharmaceutical composition is formulated for oral administration. Such formulations may be prepared by any method known in the art of pharmacy.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art.

In the invention, the method and composition/pharmaceutical composition are effective in treating a virus infection. Exemplified viruses which are responsive include, without limitation, a hepatitis virus, an influenza virus, a herpes simplex virus, an enterovirus, a rotavirus, a dengue virus, a poxvirus, a human immunodeficiency virusor, an adenovirus, a coronavirus infection, an arenavirus infection, a measles virus, or a Norovirus. Preferably, the viral infection is a hepatitis virus infection. More preferably, the viral infection is a hepatitis virus B infection, a hepatitis virus C infection, or a hepatitis virus D infection. Most preferably, the viral infection is a hepatitis virus B infection.

In another aspect, the viral infection is preferably a herpes simplex virus infection.

The present invention is further illustrated by the following examples, which are provided for the purpose of demonstration rather than limitation.

EXAMPLES

Example 1 Preparation of an Extract of *Antrodia camphorata* and its Active Fraction 100 grams of *Antrodia camphorata* fruiting body was heat-recirculated with methanol for 6 hours, and the extract was collected and dried under reduced pressure to obtain 15 grams of the *Antrodia camphorate* methanol extract.

15 grams of the *Antrodia camphorata* methanol extract as obtained above was taken, filled with silicon dioxide, and subjected to a gradient elution with the eluant "hexane/ethyl acetate/methanol" in a column separation (3×12 cm) to obtain active fractions, including A2 (*Antrodia camphorata* extracts), A3 (dehydrosulphurenic acid), A4 (antcin K), A5 (versisponic acid), and A6 (dehydroeburicoic acid).

Example 2 Effects of *Antrodia camphorata* Extracts on HBV Infection 2.1 Materials and Methods
2.1.1 HepG2.2.15 Cells Continuous HBV proliferation can be achieved in HepG2.2.15 cells (RRID:CVCL_L855) stably transfected with the HBV genome of the adw2 subtype. HepG2.2.15 cells are used because of the unlimited supply and constant quality and were maintained in Dulbecco's modified Eagle medium (DMEM; Invitrogen) supplemented with 10% heat-inactivated fetal bovine serum (FBS; Thermo) plus 100 units of penicillin and 100 □g of streptomycin per ml (both from Invitrogen).

2.1.2 HuS-E/2 Cells

HuS-E/2 cells that retains primary hepatocyte characteristics even after prolonged culture are utilized for HBV infection. For HBV infection, HuS-E/2 cells were differentiated with 2% DMSO for 7 days, and virus particles were collected to infect and replicate in HuS-E/2 cells as described in our previous study [25]. These cells are useful to assay infectivity of HBV strains, and screening of anti-HBV agents.

2.1.3 Collection of HBV Particles

The culture medium from drug-treated HepG2.2.15 cells is clarified by centrifugation at 1,000×g at 4° C. for 10 min, and then the supernatant is layered on top of a 20% sucrose cushion (20% sucrose, 20 mM HEPES, pH 7.4, 0.1% bovine serum albumin [BSA]) and centrifuged at 197,000×g for 3 h at 4° C. to pellet the HBV particles, which are then concentrated 100 fold to detect HBV DNA.

2.1.4 DNA and RNA Isolation, Reverse Transcription and Real-Time PCR

Total DNA is extracted with a Genomic DNA isolation kit (Nexttec Biotechnologie, Germany). Total RNA is isolated from cultured cells using TRIzol® reagent (Invitrogen). Reverse transcription is performed with the RNA templates, AMV reverse transcriptase (Roche), and oligo-dT primer. The products are subjected to real-time PCR with primer sets of specific genes and SYBR Green PCR Master Mix (Bio-Rad). The primer sets used for HBV core, HBsAg, cccDNA and GAPDH are described [25]. The results are analyzed with the iCycler iQ real-time PCR detection system (Bio-Rad). Plasmid p1.3HBcl is prepared at 10-fold dilutions ($2*10^4$-$2*10^9$ copies/imp to generate a standard curve in parallel PCR reactions.

2.1.5 Enzyme-Linked Immunosorbent Assay (ELISA)

The HBsAg and HBeAg ELISA Kit (General Biologicals Corp.) are used to detect hepatitis B surface antigen (HBsAg) and hepatitis B core antigen (HBeAg) with the protocol suggested.

2.1.6 Statistical Analysis

All values are expressed as mean±SE. Each value is the mean of at least three experiments in each drug in vitro experiments. Student's t-test is used for statistical comparison. * indicates that the values are significantly different from the control (*, p<0.05;  P<0.01; *, P<0.001).

2.2 Cell Viability of *Antrodia camphorata* Fruit Body Extracts

Figure 1B:
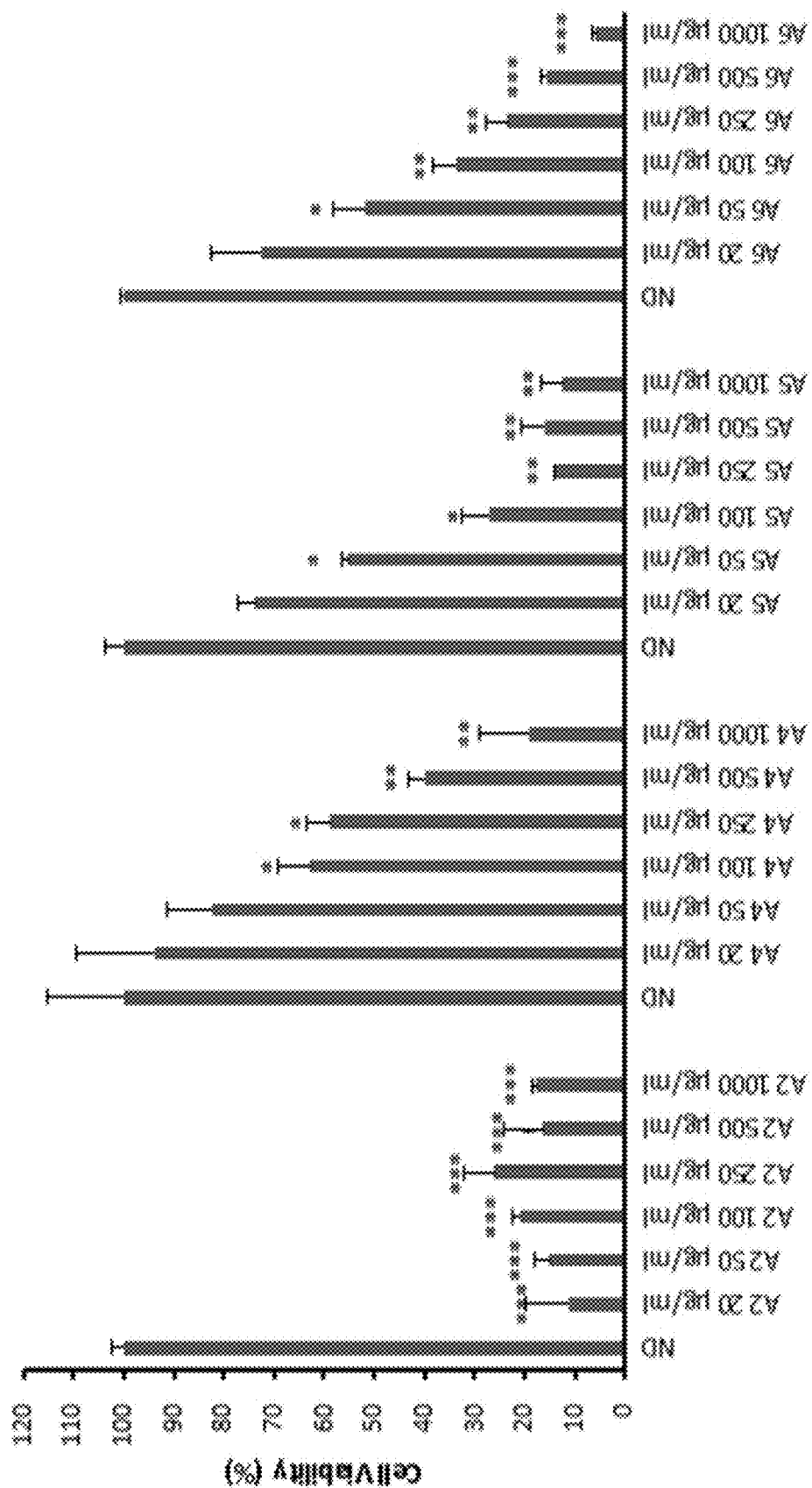
FIG. 1B shows an effect of *Antrodia camphorata* fruit body extracts on cell viability. HuS-E/2 cells were treated with 0-1000 μg/ml *Antrodia camphorata* fruit body extracts for 48 h, then the MTT assay was performed to detect cell viability. *, P<0.05; , P<0.01; *, P<0.001.

The *Antrodia camphorata* fruit body extracts used were A2 (*Antrodia camphorata* extracts), A4 (antcin K), A5 (versisponic acid), and A6 (dehydroeburicoic acid). Before testing their potential antiviral effect on HBV infection, we first examined their toxicity for HepG2.2.15 cells and HuS-E/2 immortalized human primary hepatocytes cells at concentration from 20 to 1000 μg/ml. As shown in FIG. 1, in HepG2.2.15 cells, 50 μg/ml A2, 50 μg/ml A4, and 20 μg/ml A5 had little or no toxic effect. Toxicity of A6 was seen at 20 □g/ml. In HuS-E/2 cells, toxicity of A2 was seen at 20 □g/ml. 50 μg/ml A4, 20 μg/ml A5, and 20 μg/ml A6 had no toxic effect. Therefore, the concentrations indicated in Table 1 and Table 2 were used in subsequent studies.

TABLE 1

| HepG2.2.15 cells | Dose 1 (μg/ml) | Dose 2 (μg/ml) |
| --- | --- | --- |
| A2 | 20 | 50 |
| A4 | 20 | 50 |
| A5 | 10 | 20 |
| A6 | 5 | 10 |

TABLE 2

| HuS-E/2 cells | Dose 1 (μg/ml) | Dose 2 (μg/ml) |
| --- | --- | --- |
| A2 | 5 | 10 |
| A4 | 20 | 50 |
| A5 | 10 | 20 |
| A6 | 10 | 20 |

Figure 2A:
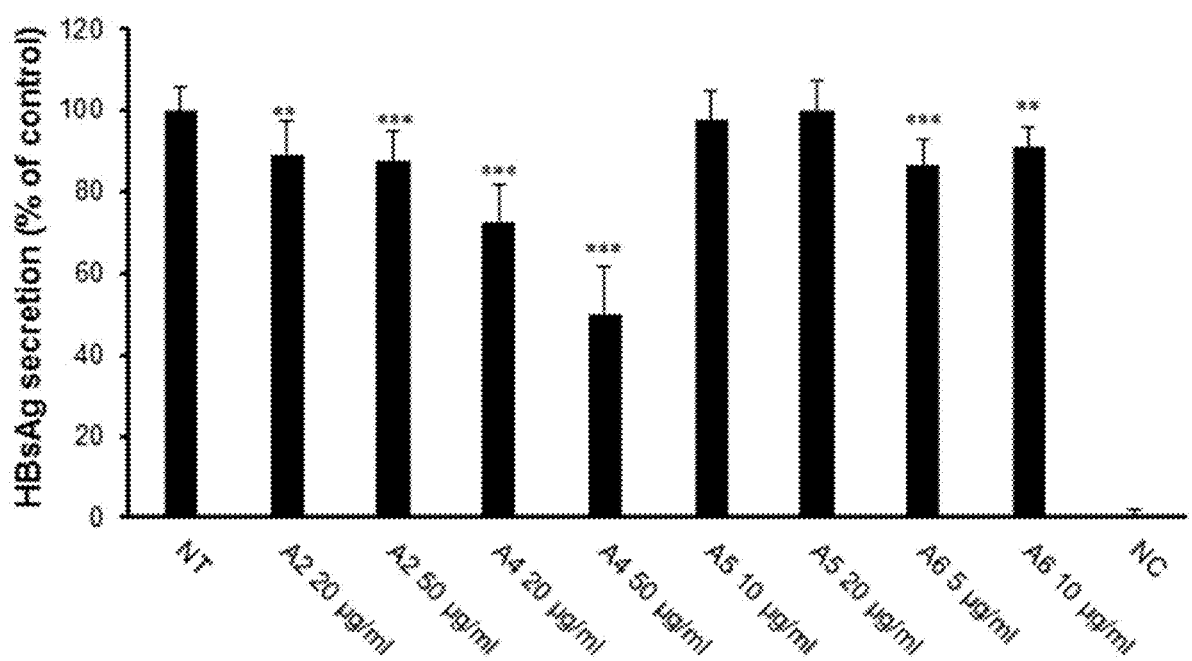
FIG. 2A shows an effect of *Antrodia camphorata* fruit body extracts on HBV replication. HepG2.2.15 cells were cultured with different concentrations of *Antrodia camphorata* fruit body extracts for 48 h, then the culture medium was collected to measure HBV HBsAg by ELISA. HepG2, containing no HBV, was used as a negative control (NC). The results are expressed as a percentage of the non-drug-treated positive control (NT) and are shown as mean±SD for three independent experiments. *, P<0.05; , P<0.01; *, P<0.001.
Figure 2B:
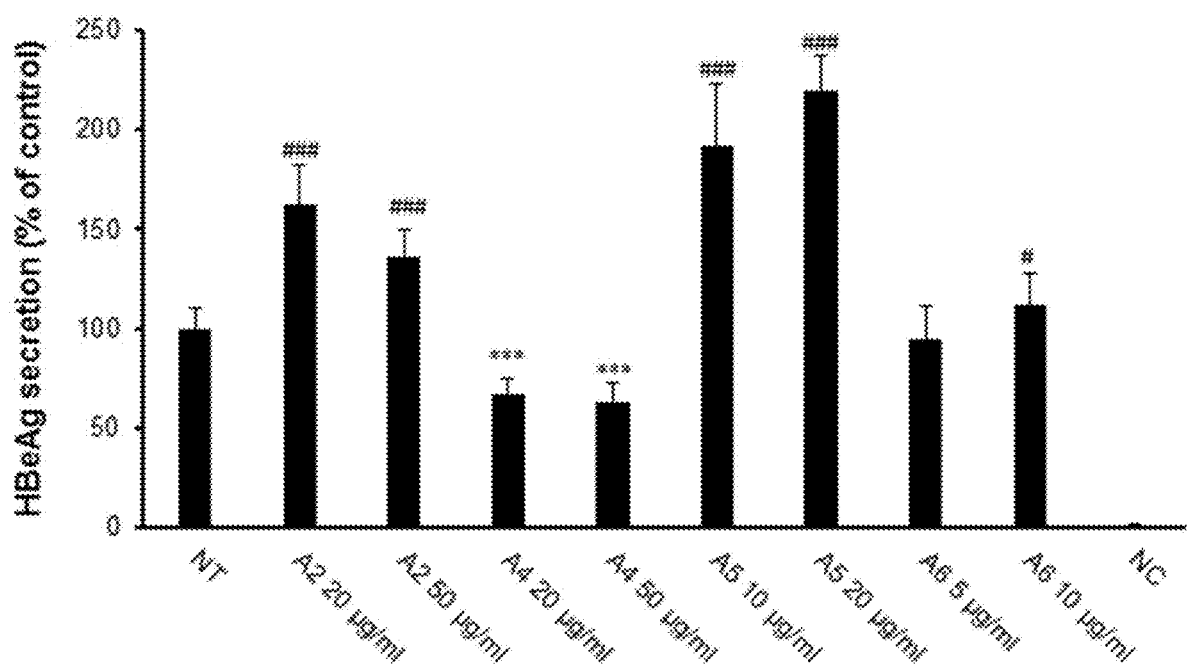
FIG. 2B shows an effect of *Antrodia camphorata* fruit body extracts on HBV assembly. HepG2.2.15 cells were cultured with different concentrations of *Antrodia camphorata* fruit body extracts for 48 h, then the culture medium was collected to measure HBV HBeAg by ELISA. HepG2, containing no HBV, was used as a negative control (NC). The results are expressed as a percentage of the non-drug-treated positive control (NT) and are shown as mean±SD for three independent experiments. *, P<0.05; , P<0.01; *, P<0.001.
Figure 2C:
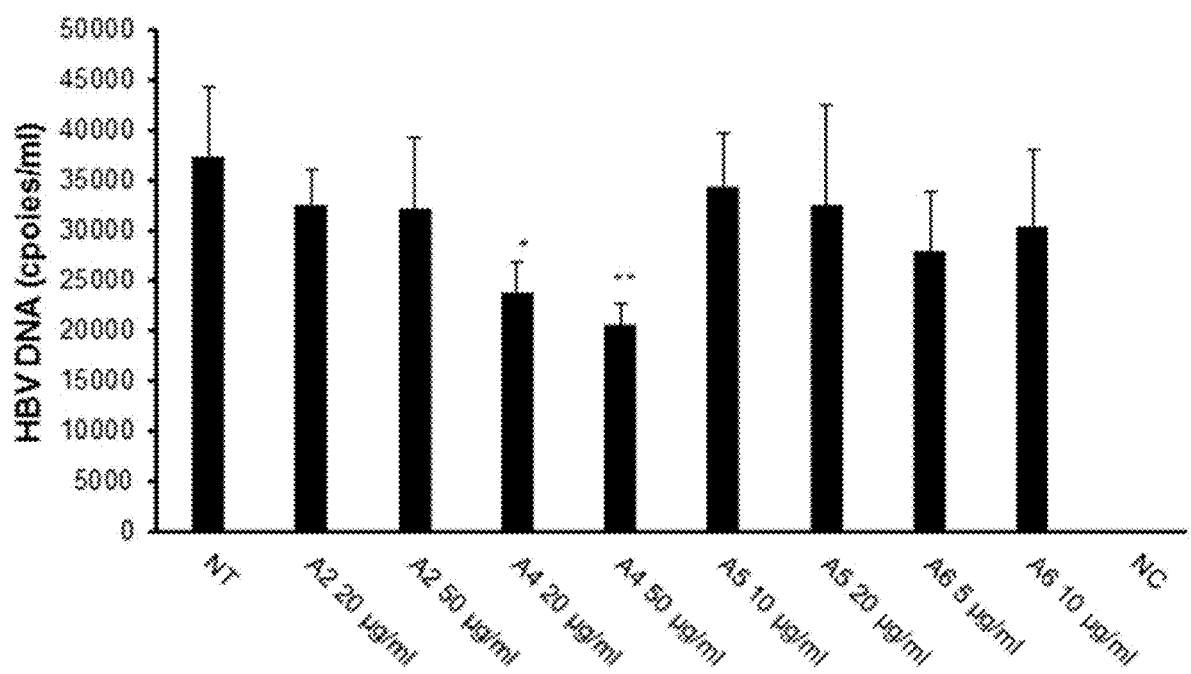
FIG. 2C shows an effect of *Antrodia camphorata* fruit body extracts on HBV release. HepG2.2.15 cells were cultured with different concentrations of *Antrodia camphorata* fruit body extracts for 48 h, then the culture medium was collected to measure HBV DNA by real-time PCR. Plasmid p1.3HBcl, which contains a 1.3-fold HBV genome (ayw subtype (Galibert et al., 1979)), was used as standard in parallel PCR reactions, while HepG2, containing no HBV, was used as a negative control (NC). The results are expressed as a percentage of the non-drug-treated positive control (NT) and are shown as mean±SD for three independent experiments. *, P<0.05; , P<0.01; *, P<0.001.

2.3 Inhibitory Effect of *Antrodia camphorata* Fruit Body Extracts on HBV Infection in HepG2.2.15 Cells To test whether *Antrodia camphorata* fruit body extracts had any effect on HBV genome replication, assembly, or secretion, HepG2.2.15 cells, which stably transfected with HBV genome, were used to incubate with four *Antrodia camphorata* fruit body extracts for 48 hours, then HBsAg, HBeAg and HBV DNA collected from medium were measured by ELISA and real-time PCR. Interestingly, ELISA results showed that levels of HBsAg (FIG. 2A) and HBeAg (FIG. 2B) in the culture supernatant, which reflects the quantity of secreted HBV particles, was significantly decreased to about 50-60% in the presence of A4 drug at 20 μg/ml and 50 μg/ml. In addition, as shown in FIG. 2C, HBV DNA was also repressed to 55% in the treatment of A4 drug at 50 μg/ml.

Figure 3A:
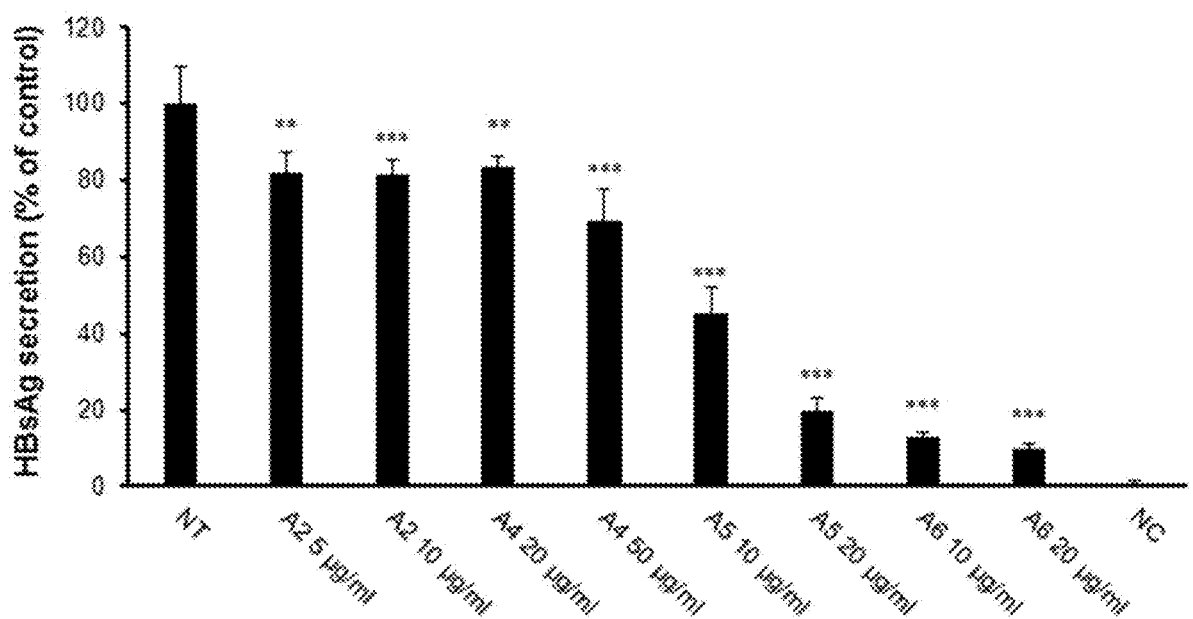
FIG. 3A shows an effect of *Antrodia camphorata* fruit body extracts on HBV entry. DMSO-differentiated HuS-E/2 cells were exposed to HBV at a MOI of 10 for 20 h in the presence of the indicated concentration of *Antrodia camphorata* fruit body extracts, then the HBV and drugs were removed and the cells incubated for 2 days, when HBsAg secreted into the culture medium was measured by ELISA and expressed as a percentage of the value for the non-drug-treated controls. The results are the mean±SD for three independent experiments. *, P<0.05; , P<0.01; *, P<0.001.
Figure 3B:
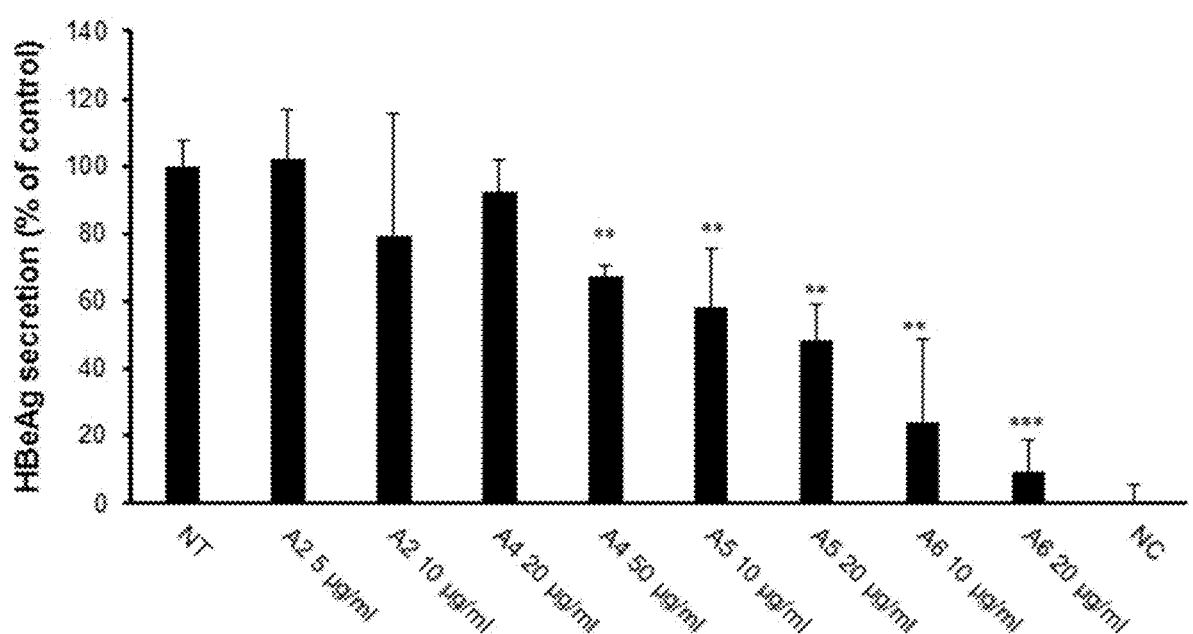
FIG. 3B shows an effect of *Antrodia camphorata* fruit body extracts on HBV entry. DMSO-differentiated HuS-E/2 cells were exposed to HBV at a MOI of 10 for 20 h in the presence of the indicated concentration of *Antrodia camphorata* fruit body extracts, then the HBV and drugs were removed and the cells incubated for 2 days, when HBeAg secreted into the culture medium was measured by ELISA and expressed as a percentage of the value for the non-drug-treated controls. The results are the mean±SD for three independent experiments. *, P<0.05; , P<0.01; *, P<0.001.
Figure 3C:
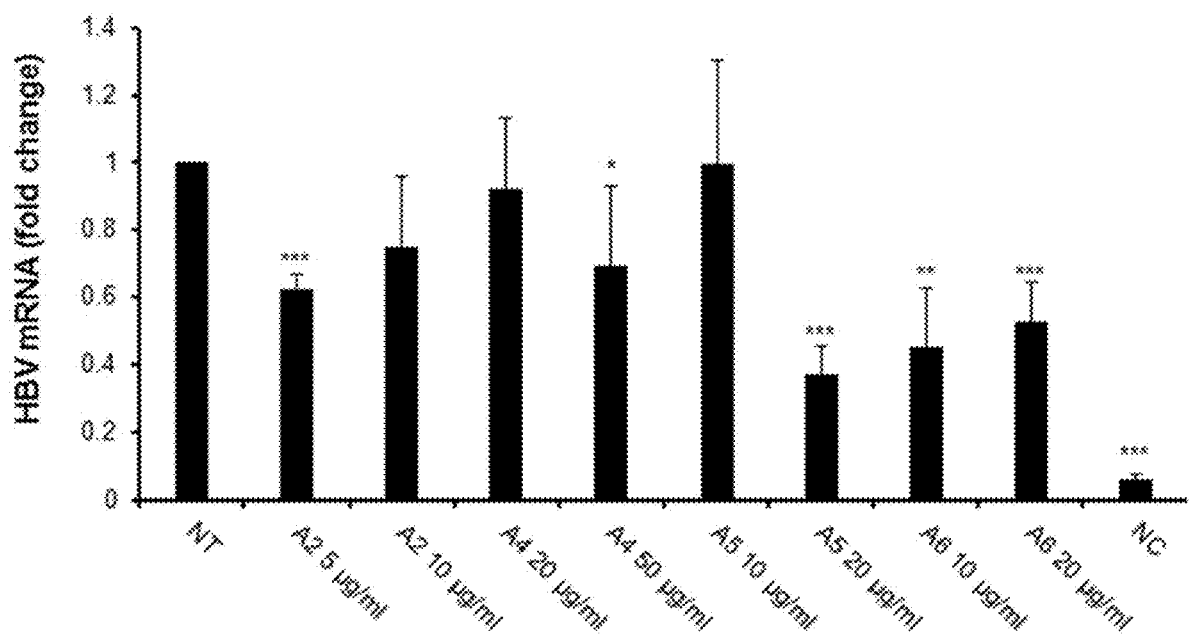
FIG. 3C shows an effect of *Antrodia camphorata* fruit body extracts on HBV entry. DMSO-differentiated HuS-E/2 cells were exposed to HBV at a MOI of 10 for 20 h in the presence of the indicated concentration of *Antrodia camphorata* fruit body extracts, then the HBV and drugs were removed and the cells incubated for 2 days. RNA was then extracted from cells and subjected to RT-PCR to measure HBV mRNA levels. The results expressed were as a percentage of the value for the non-drug-treated cells. Control PCRs were performed for endogenous GAPDH mRNA as the loading control. The results are the mean±SD for three independent experiments. *, P<0.05; , P<0.01; *, P<0.001.

2.4 Inhibitory Effect of *Antrodia camphorata* Fruit Body Extracts on HBV Entry in HuS-E/2 Cells To evaluate the effects of *Antrodia camphorata* fruit body extracts on HBV infectivity and replication, HuS-E/2 cells were infected with ayw subtype HBV derived from HepG2.2.15 cells. The different *Antrodia camphorata* fruit body extracts were added to the medium during infection with HBV for 18 h, then the infected cells were washed and incubated in fresh medium for 48 hours, when HBsAg and HBeAg in culture medium were detected by ELISA and HBV mRNA was detected by real-time PCR as an index of efficiency of HBV infection. Interestingly, a greater than 80% decrease in HBV HBsAg and HBeAg levels was observed in cells treated with A5 and A6 drugs at 20 μg/ml, while the other compounds had a lower effect or no effect (FIGS. 3A and B). The presence of A5 and A6 drugs during infection resulted in a decrease in levels of HBV mRNA (FIG. 3C).

In this study, HepG2.2.15 cells which was stably expressed HBV genome were used to detect the effect of *Antrodia camphorata* fruit body extract on HBV morphogenesis. These results showed that A4 drug significantly inhibits HBV replication, the assembly or release of viral particles. A marked dose-dependent reduction in HBsAg protein and core protein levels (FIGS. 2A and 2B) and HBV DNA in particles was seen with the treatment of A4 (FIG. 2C).

On the other hand, to test whether *Antrodia camphorata* fruit body extracts had an effect on HBV entry, HuS-E/2 cells were used to detect the effect of *Antrodia camphorata* fruit body extracts on HBV infection. When HuS-E/2 cells were exposed to HBV, A5 and A6 were much more effective at inhibiting the entry of HBV into HuS-E/2 cells by decrease in HBV HBsAg, HBeAg, and HBV mRNA expression levels (FIGS. 3A, 3B and 3C). Together, these results show that HBV infection was profoundly reduced by either A4, A5 and A6 treatment at different steps during HBV infection.

Figure 4:
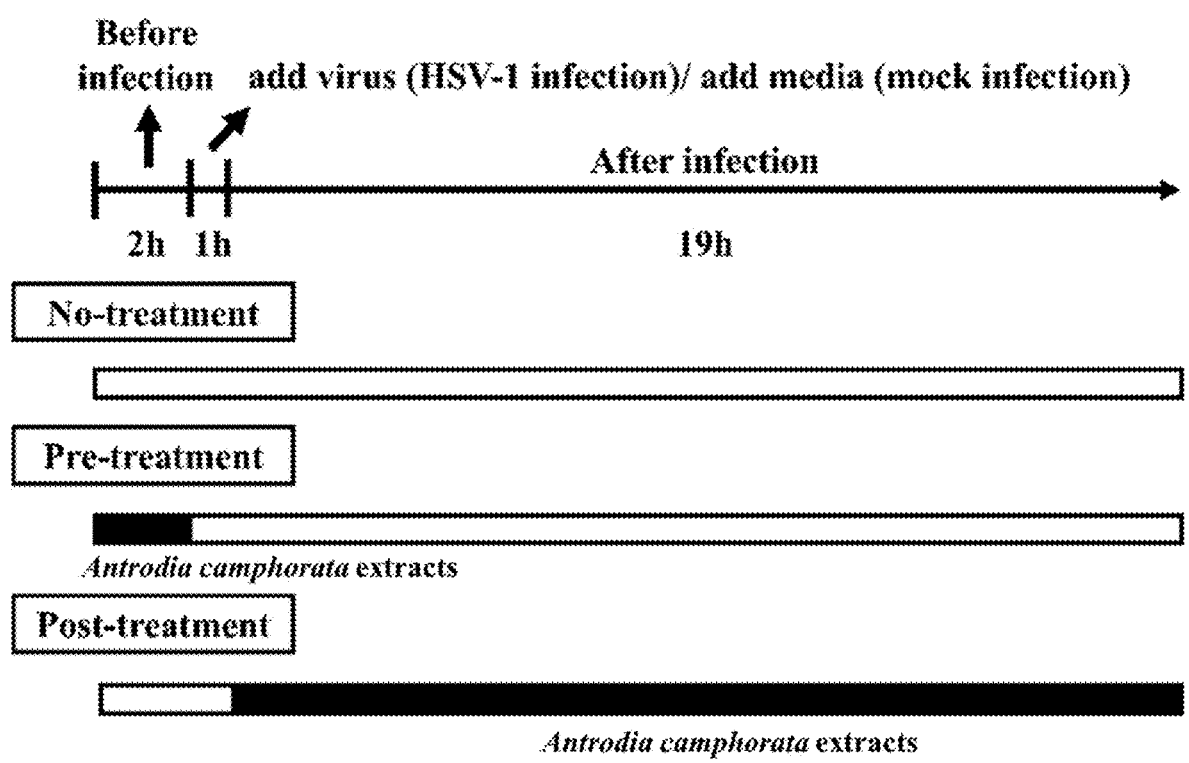
FIG. 4 provides Experimental conditions for evaluation of the effects of *Antrodia camphorata* fruit body extracts on oral epithelial cells during HSV-1 infection. Three experimental conditions, including no-treatment, pre-treatment and post-treatment were performed. Oral epithelial cells (OC3) were pre-treated with media only or media containing each *Antrodia camphorata* extracts for 2 hours, followed by HSV-1 inoculation. Cells were infected with HSV-1 viruses at multiplicity of infection (MOI) of 5 or mock infected for 1 hour at 37° C. for viral entry to occur. *Antrodia camphorata* extracts were not added during viral inoculation for 1 hour to avoid of its direct effects on virions. Mock- or HSV-1-infected cells were further incubated in the absence or presence of the drug for 19 hours.

Example 3 Effects of *Antrodia camphorata* Extracts on HSV Infection 3.1 Materials and Methods 3.1.1 Experiment Design The oral epithelial cell line (OC3) was used to determine the possible effects of *Antrodia camphorata* extracts on oral epithelial cells during HSV-1 infection. Cell monolayers were treated as illustrated in FIG. 4 (please also see details in the Materials and Methods section). Three experimental conditions, including no-treatment, pre-treatment and post-treatment were performed. Whether these *Antrodia campho-*

*rata* extracts have effects before or after viral infection were examined. The effects of *Antrodia camphorata* extracts on viral propagation (viral yields) in infected oral epithelial cells were examined. At 19-20 h post infection, viral yields in the supernatants were determined using the plaque assay. Viability of treated cells was also determined using the MTT assay for the mitochondrial dehydrogenase activity. Moreover, purified HSV-1 virions were directly treated with *Antrodia camphorata* extracts to examine whether *Antrodia camphorata* extracts exert anti-HSV-1 activity directly on virus particles before viral entry.

3.1.2 Oral Cell Cultures

Oral carcinoma 3 (OC3) cells, established from an areca chewing/non-smoking patient [26], were cultured in a medium composed of Dulbecco's modified eagle medium (DMEM) containing 10% heat inactivated fetal bovine serum (FBS) and KSFM in a 1:2 ratio. KSFM is the epithelial serum-free medium (Gibco BRL Laboratories) supplemented with recombinant epidermal growth factor (0.1-0.2 ng/ml) and bovine pituitary extract (20-30 μg/ml). African green monkey kidney (Vero) cells were propagated in DMEM supplemented with 5% FBS. All of the growth media were supplemented with the antibiotic-antimycotic solution, 100 units/ml penicillin G sodium, 100 μg/ml streptomycin sulfate and 0.25 μg/ml amphotericin B (Gibco BRL Laboratories, Grand Island, N.Y.).

3.1.3 HSV Virus Preparation

HSV-1 virus (KOS strain) from the extra-cellular fluid of infected Vero cells was purified using sucrose-gradient. Purified viruses were stored frozen in small aliquots. Purified viruses were titered using the plaque assay.

3.1.4 Infection Conditions

Oral epithelial cells (OC3 cells) were infected with HSV-1 at multiplicity of infection (MOI) of 5 or mock infected for 1 h at 37° C. for viral entry to occur. Unbound viruses were removed. Infected cells were then overlaid with appropriate media and incubated at 37° C. The *Antrodia camphorata* fruit body extracts used were A2 (*Antrodia camphorata* extracts), A3 (dehydrosulphurenic acid), A4 (antcin K), A5 (versisponic acid), and A6 (dehydroeburicoic acid). For the effects of *Antrodia camphorata* fruit body extracts, oral cells were treated in three different experimental conditions (FIG. 1): (1) no treatment, (2) pre-treatment with each *Antrodia camphorata* fruit body extracts before infection and (3) post-treatment with each *Antrodia camphorata* fruit body extracts after infection. Purified HSV-1 virions were also incubated directly with media only or media containing *Antrodia camphorata* fruit body extracts. The viral infectivity of treated virions was then examined using the plaque assay.

3.1.5 MTT Assay for the Mitochondrial Dehydrogenase Activity

The mitochondrial dehydrogenase activity of treated cells was evaluated using the FBS-free medium containing 1 mg/ml of 3-[4,5-dimethylthiazol-2-yl]-2,5 diphenyltetrazolium bromide (MTT). After 4 h of incubation at 37° C., the media were discarded and the formazan blue, which formed by reacting MTT with mitochondrial dehydrogenase in the living cells, was dissolved with DMSO. The optical density (OD) was measured at 570 nm. The background signal inherent to the plates when no cell was present was subtracted from the absorbance obtained from each sample.

3.1.6 Plaque Assay for the Viral Titers

Viral titers in the supernatants after infection were determined using the plaque assay. Cells were grown to confluence and infected with tenfold serial dilution of the samples. Cells were then overlaid with medium containing 3% carboxymethylcellulose to prevent the formation of secondary plaques. Cells were incubated until well-defined clear plaques were formed. Cells were fixed with 3.7% formaldehyde and stained with crystal violet. Plaques were observed and counted under an inverted microscope. The viral yield of the media-pretreated HSV-1 infected control was considered to be 100%.

3.1.7 Statistical Analysis

Each experiment was repeated at least three times to ensure reproducibility. The data were calculated for mean and standard error of the mean (SEM). The one-way ANOVA was used to identify statistically significant differences. A level of $p<0.05$ was considered significantly different.

Figure 5:
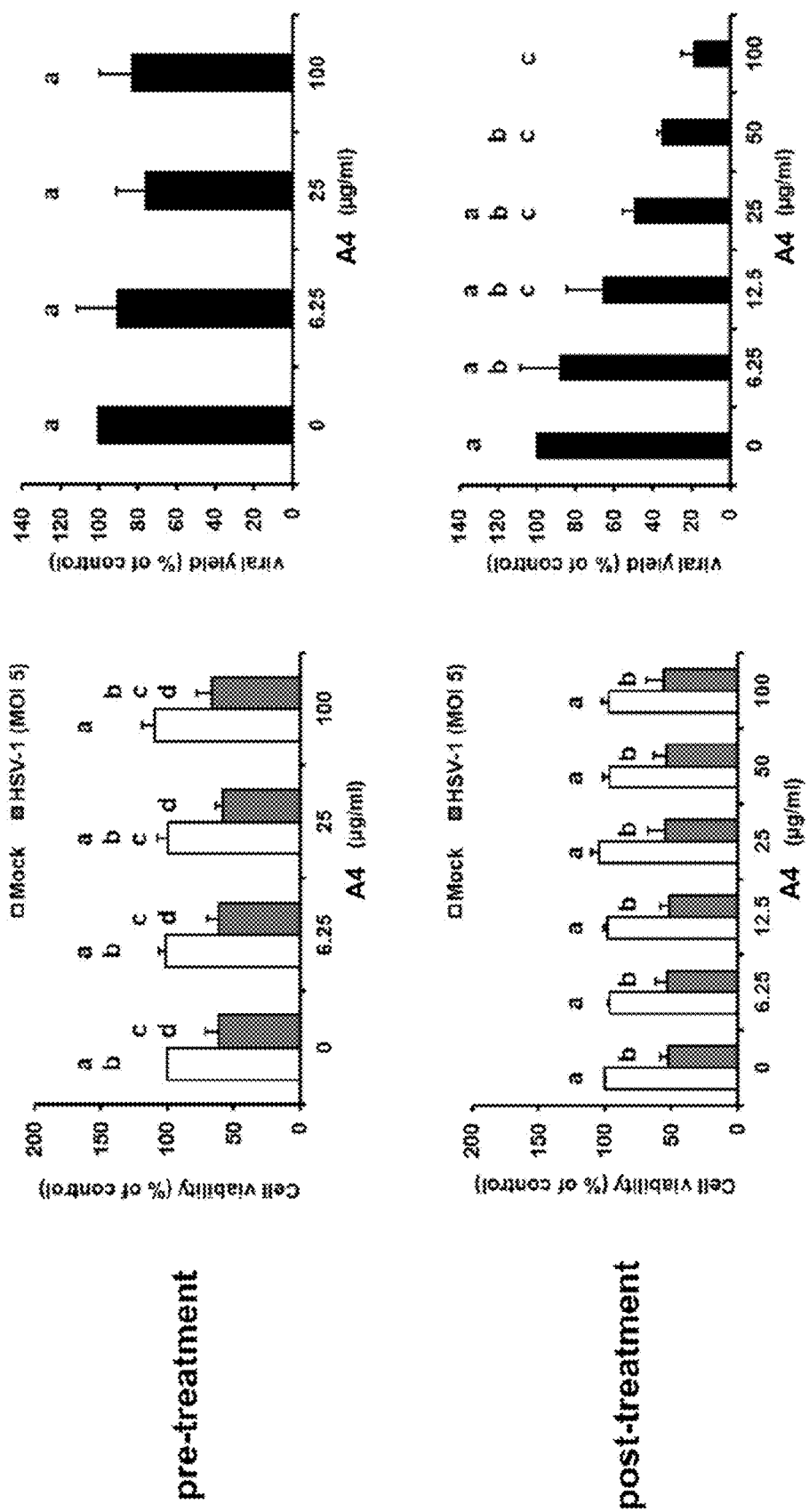
FIG. 5 shows effects of A4 (antcin K) on cell viability and viral propagation in oral epithelial cells after HSV-1 infection. Oral epithelial cells (OC3) were incubated with various concentrations of A4 in experimental conditions as illustrated in FIG. 1. At 19 hours post infection, the cell viability was tested for the mitochondrial dehydrogenase activity using the MTT assay. The percentages of cell viability relative to that in the control are shown. The viability of the mock-infected culture medium control was considered to be 100%. Moreover, viral yields in the supernatants were examined using the plaque assay. The viral yield from the media treated control group was considered to be 100%. The results shown are the mean±standard error of the mean (SEM) from at least three independent experiments. Statistical differences are shown by different lowercase letters (analysis of variance, Tukey, $\alpha=0.05$). Two samples were statistically different if indicated with completely different lowercase letters.

3.2 Effects of *Antrodia camphorata* Fruit Body Extracts on Cell Viability and Viral Propagation in Oral Epithelial Cells After HSV-1 Infection The effects of *Antrodia camphorata* fruit body extracts [(A2 (*Antrodia camphorata* extracts), A3 (dehydrosulphurenic acid), A4 (antcin K), A5 (versisponic acid), and A6 (dehydroeburicoic acid)] on cell viability and viral propagation were evaluated. The viability of mock-infected cells or HSV-1 infected cells was not affected evidently by A4 (FIG. 5). Pre-treatment of OC3 cells with A4 had little effects on the viral yields. However, post-treatment of OC3 cells with A4 significantly reduced viral yields in the supernatants in a dose-dependent manner. The averaged viral yield was reduced to 19% when infected cells were post-treated with 100 μg/ml of A4.

Figure 6:
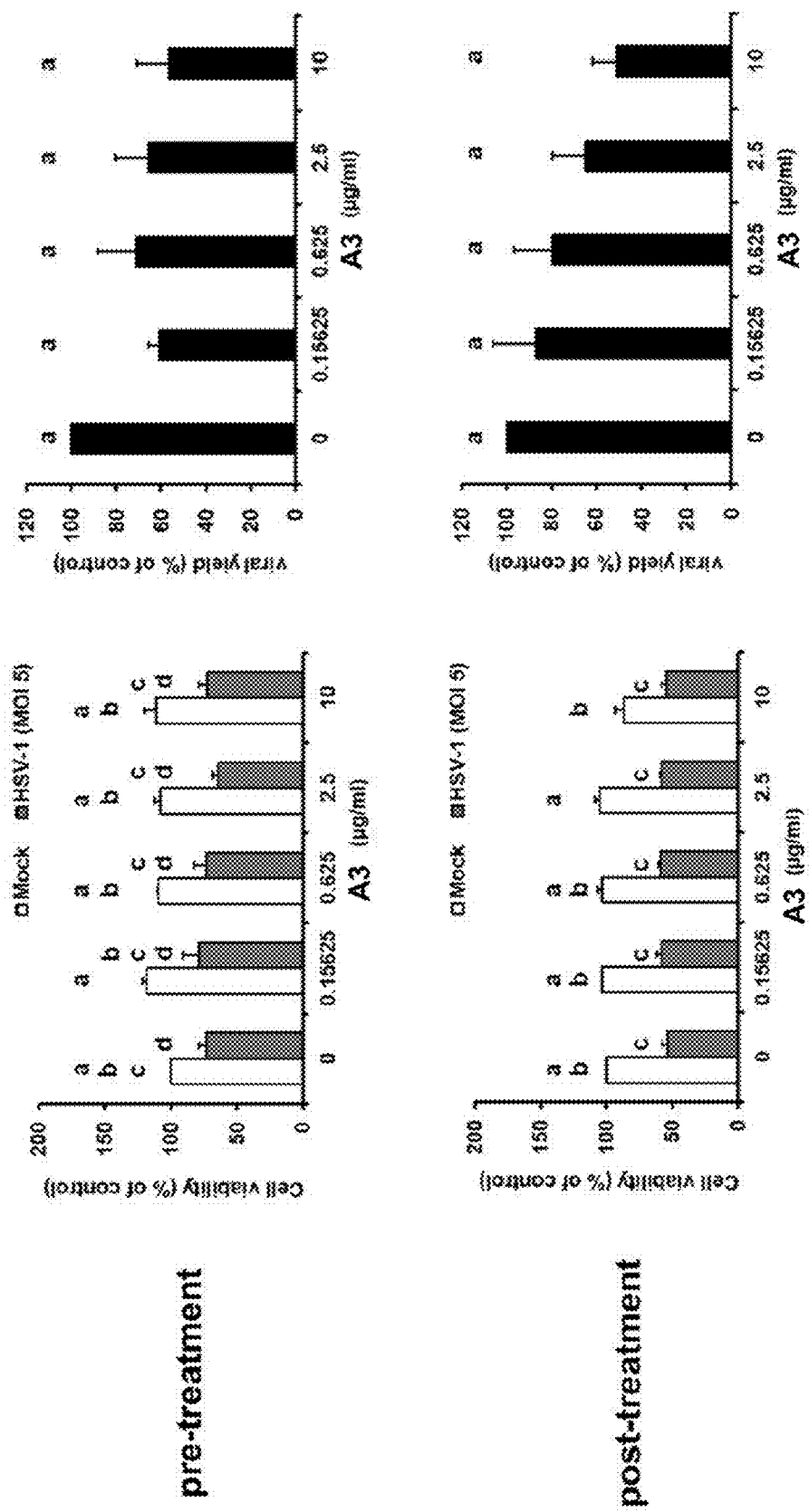
FIG. 6 shows effects of A3 (dehydrosulphurenic acid) on cell viability and viral propagation in oral epithelial cell safter HSV-1 infection. OC3 cells were incubated with various concentrations of A3 in experimental conditions as illustrated in FIG. 4. At 19 hours post infection, the cell viability was tested using the MTT assay. The percentages of cell viability relative to that in the control are shown. The viability of the mock-infected culture medium control was considered to be 100%. Moreover, viral yields in the supernatants were examined using the plaque assay. The viral yield from the media treated control group was considered to be 100%. The results shown are the mean±SEM from at least three independent experiments. Statistical differences are shown by different lowercase letters (analysis of variance, Tukey, $\alpha=0.05$). Two samples were statistically different if indicated with completely different lowercase letters.

The viability of mock-infected cells or HSV-1 infected cells was not affected evidently by A3 (FIG. 6). The viral yield was reduced to 57% when cells were pre-treated with 10 μg/ml of A3 for 2 hours before HSV-1 infection (FIG. 6). Moreover, the viral yield was reduced to 65% when cells were post-treated with 2.5 μg/ml of A3 after HSV-1 infection (FIG. 6). However, the reduction did not reach statistical difference.

Figure 7:
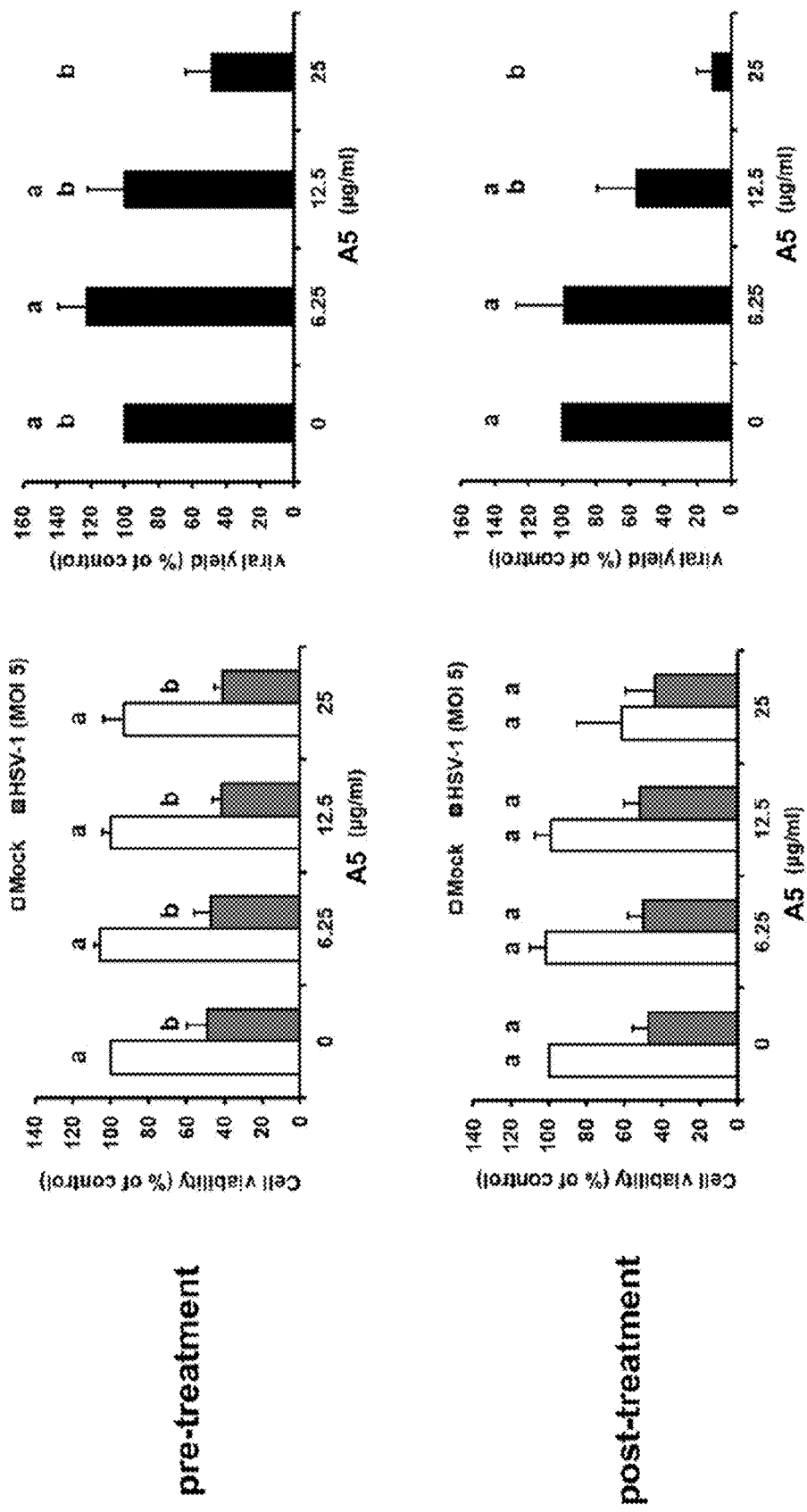
FIG. 7 shows effects of A5 (versisponic acid) on cell viability and viral propagation in oral epithelial cells after HSV-1 infection. OC3 cells were incubated with various concentrations of A5 in experimental conditions as illustrated in FIG. 4. At 19 hours post infection, the cell viability was tested using the MTT assay. The percentages of cell viability relative to that in the control are shown. The viability of the mock-infected culture medium control was considered to be 100%. Moreover, viral yields in the supernatants were examined using the plaque assay. The viral yield from the media treated control group was considered to be 100%. The results shown are the mean±SEM from at least three independent experiments. Statistical differences are shown by different lowercase letters (analysis of variance, Tukey, $\alpha=0.05$). Two samples were statistically different if indicated with completely different lowercase letters.

The viability of mock-infected cells or HSV-1 infected cells was not affected evidently by A5 (FIG. 7). Pre-treatment and post-treatment of OC3 cells with A5 significantly reduced viral yields in the supernatants in a dose-dependent manner (FIG. 7). The viral yield was reduced to 48% when cells were pre-treated with 25 μg/ml of A5 for 2 hours before HSV-1 infection (FIG. 7). The viral yield was reduced to 57% when infected cells were post-treated with 12.5 μg/ml of A5 (FIG. 7).

Figure 8:
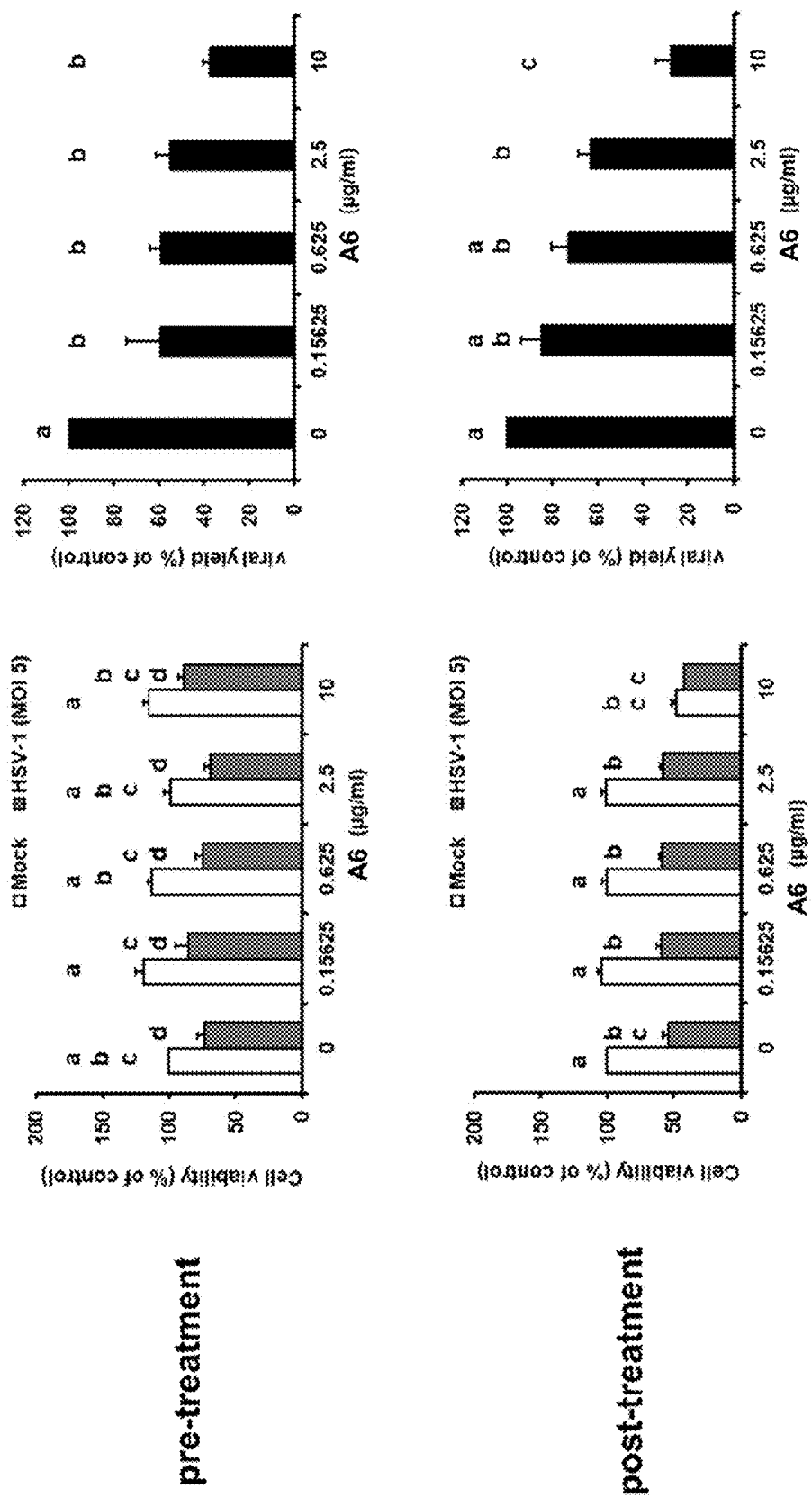
FIG. 8 shows effects of A6 (dehydroeburicoic acid) on cell viability and viral propagation in oral epithelial cells after HSV-1 infection. OC3 cells were incubated with various concentrations of A6 in experimental conditions as illustrated in FIG. 1. At 19 hours post infection, the cell viability was tested using the MTT assay. The percentages of cell viability relative to that in the control are shown. The viability of the mock-infected culture medium control was considered to be 100%. Moreover, viral yields in the supernatants were examined using the plaque assay. The viral yield from the media treated control group was considered to be 100%. The results shown are the mean±SEM from at least three independent experiments. Statistical differences are shown by different lowercase letters (analysis of variance, Tukey, $\alpha=0.05$). Two samples were statistically different if indicated with completely different lowercase letters.

The viability of mock-infected cells was significantly reduced when cells were post-treated with 10 μg/ml of A6 for 19 hours (FIG. 8). The results suggest that 10 μg/ml of A6 may partly reduce cell viability. Pre-treatment and post-treatment of OC3 cells with A6 significantly reduced viral yields in the supernatants in a dose-dependent manner (FIG. 8). The viral yield was reduced to 37% when cells were pre-treated with 10 μg/ml of A6 for 2 hours before HSV-1 infection (FIG. 8).The viral yield was reduced to 63% when infected cells were post-treated with 2.5 μg/ml of A6 (FIG. 8).

Figure 9:
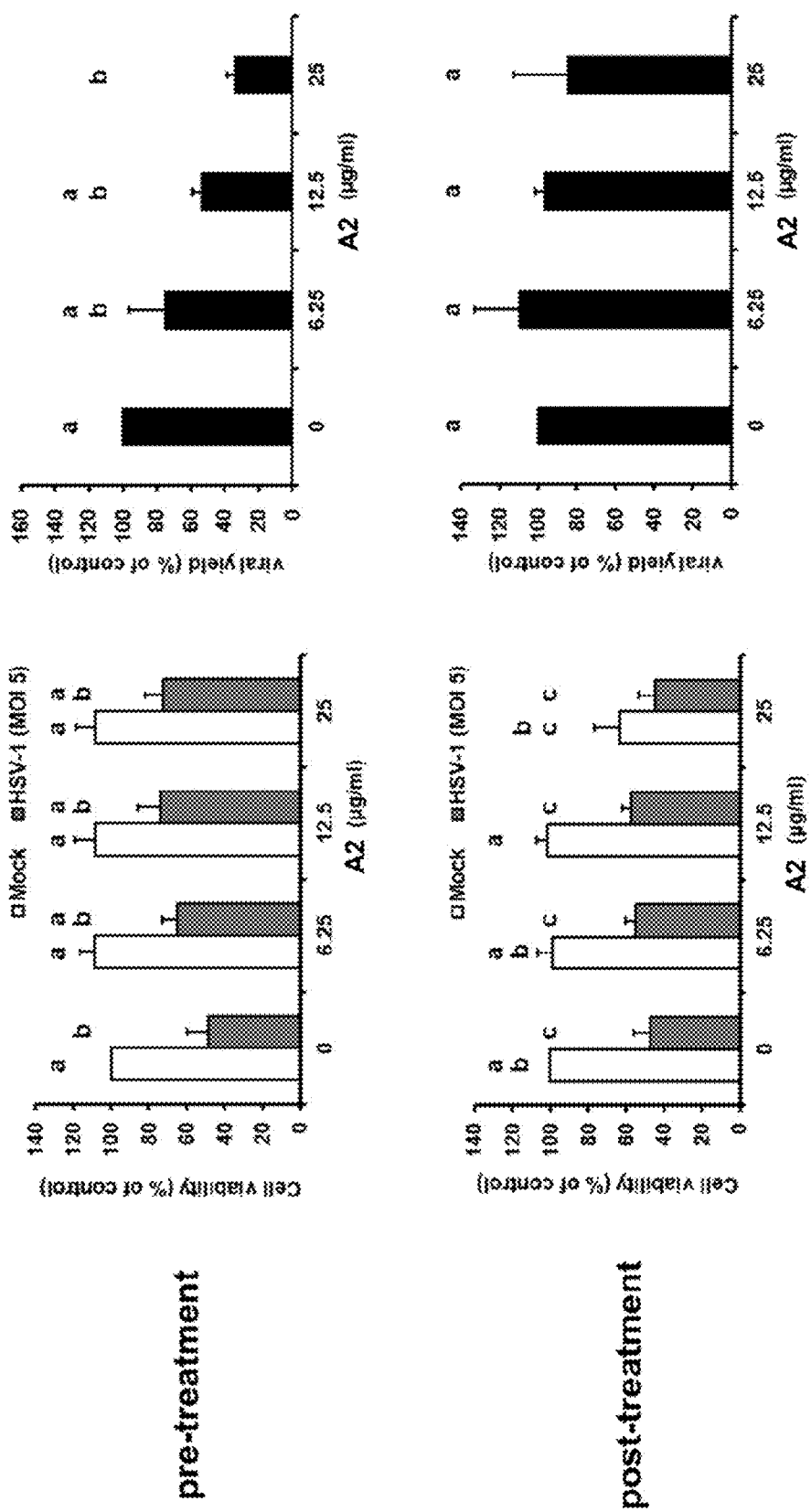
FIG. 9 shows effects of A2 (*Antrodia camphorata* extracts) on cell viability and viral propagation in oral epithelial cells after HSV-1 infection. OC3 cells were incubated with various concentrations of A2 in experimental conditions as illustrated in FIG. 4. At 19 hours post infection, the cell viability was tested using the MTT assay. The percentages of cell viability relative to that in the control are shown. The viability of the mock-infected culture medium control was considered to be 100%. Moreover, viral yields in the supernatants were examined using the plaque assay. The viral yield from the media treated control group was considered to be 100%. The results shown are the mean±SEM from at least three independent experiments. Statistical differences are shown by different lowercase letters (analysis of variance, Tukey, $\alpha=0.05$). Two samples were statistically different if indicated with completely different lowercase letters.

The viability of mock-infected cells was reduced when cells were post-treated with 25 μg/ml of A2 for 19 hours (FIG. 9). Pre-treatment of OC3 cells with A2 significantly reduced viral yields in the supernatants in a dose-dependent manner. However, post-treatment of OC3 cells with A2 had little effects on the viral yields.

Figure 10:
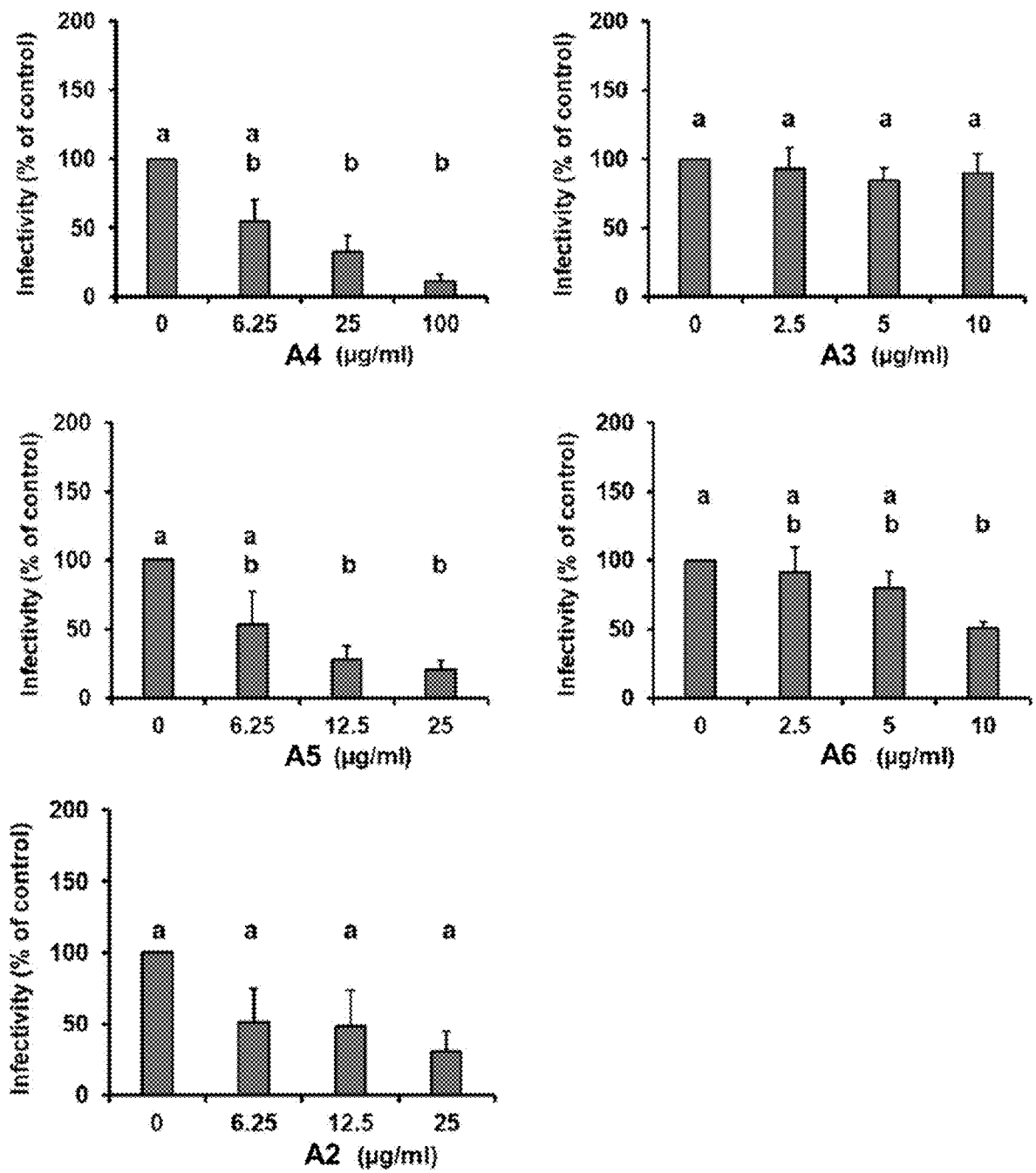
FIG. 10 shows effects of *Antrodia camphorata* extracts on HSV-1 virions. Purified HSV-1 was incubated directly with media containing various concentrations of each *Antrodia camphorata* extracts for 1 hour at 37° C. The viral titers were then examined in oral epithelial cells (OC3) using the plaque assay. The results shown are the mean±SEM from at least three independent experiments. Statistical differences are shown by different lowercase letters (analysis of variance, Tukey, $\alpha=0.05$). Two samples were significantly different if indicated with completely different lowercase letters.

3.3 Direct Effects of *Antrodia camphorata* Fruit Body Extracts on Infectivity of HSV-1 Virions Purified HSV-1 virions were incubated directly with media only or media containing various concentrations of each *Antrodia camphorata* fruit body extracts. The viral infectivity of treated virions was then examined using the plaque assay. The results showed that viral infectivity was statistically significantly inhibited by A4, A5, A6, in a dose-dependent manner (FIG. 10), suggesting that these drugs exert anti-HSV-1 activities directly on virus particles before viral entry. The most effective concentrations on HSV-1 virions were summarized in Table 4. Viral infectivity was also reduced to 30% or 41% when 25 μg/ml of A2 was used, respectively (FIG. 10).

Together, effects of *Antrodia camphorata* fruit body extracts on HSV-1 infection were varied. Pre-treatment or post-treatment of OC3 cells with *Antrodia camphorata* fruit body extracts may reduce viral yields in the supernatants. Viral infectivity was statistically significantly inhibited by A4, A5, and A6, in a dose-dependent manner.

The above description merely relates to preferred embodiments in the present invention, and it should be pointed out that, for a person of ordinary skill in the art, some improvements and modifications can also be made under the premise of not departing from the principle of the present invention, and these improvements and modifications should also be considered to be within the scope of protection of the present invention.

REFERENCES

1. Ganem, D. and A. M. Prince, Hepatitis B virus infection—natural history and clinical consequences. N Engl J Med, 2004. 350(11): p. 1118-29.
2. Beasley, R. P., Hepatitis B virus. The major etiology of hepatocellular carcinoma. Cancer, 1988. 61(10): p. 1942-56.
3. Zoulim, F. and S. Locarnini, Hepatitis B virus resistance to nucleos(t)ide analogues. Gastroenterology, 2009. 137(5): p. 1593-608 e1-2.
4. Chen, W. N. and C. J. Oon, Human hepatitis B virus mutants: significance of molecular changes. FEBS Lett, 1999. 453(3): p. 237-42.
5. Yan, H., et al., Sodium taurocholate cotransporting polypeptide is a functional receptor for human hepatitis B and D virus. Elife. 1: p. e00049.
6. Watashi, K., et al., NTCP and beyond: opening the door to unveil hepatitis B virus entry. Int J Mol Sci. 15(2): p. 2892-905.
7. Gripon, P., et al., Infection of a human hepatoma cell line by hepatitis B virus. Proc Natl Acad Sci USA, 2002. 99(24): p. 15655-60.
8. Urban, S. and P. Gripon, Inhibition of duck hepatitis B virus infection by a myristoylated pre-S peptide of the large viral surface protein. J Virol, 2002. 76(4): p. 1986-90.
9. Abou-Jaoude, G., et al., Myristoylation signal transfer from the large to the middle or the small HBV envelope protein leads to a loss of HDV particles infectivity. Virology, 2007. 365(1): p. 204-9.
10. Chai, N., et al., Assembly of hepatitis B virus envelope proteins onto a lentivirus pseudotype that infects primary human hepatocytes. J Virol, 2007. 81(20): p. 10897-904.
11. Gudima, S., et al., Primary human hepatocytes are susceptible to infection by hepatitis delta virus assembled with envelope proteins of woodchuck hepatitis virus. J Virol, 2008. 82(15): p. 7276-83.
12. Corey L, Spear P G. Infections with herpes simplex viruses. *New Engl Med* 1986; 314: 686-691.
13. Ahmed R, Morrison L A, Knipe D M. Persistence of viruses, In: Fields B N, Knipe D M, Howley P M, eds. Field's Virology. Philadelphia: Lippincott-Raven Publishers, 1996: 219-250.
14. Contreras A, Slots J. Herpesviruses in human periodontal disease. *J Periodontal Res* 2000; 35: 3-16.
15. Parra B, Slots J. Detection of human viruses in periodontal pockets using polymerase chain reaction. *Oral Microbiol Immunol* 1996; 11:289-293.
16. Ling L-J, Ho C-C, Wu C-Y, Chen Y-T, Hung S-L. Association between human herpesviruses and the severity of periodontitis. *J Periodontol* 2004; 75: 1479-1485.
17. Contreras A, Slots J. Mammalian viruses in human periodontitis. *Oral Microbiol Immunol* 1996; 11: 381-386.
18. Park N H. Virology, In: Nisengard R J, Newman M G, eds. *Oral Microbiology and Immunology*. Philadelphia: W. B. Saunders Company, 1994: 248-285.
19. Yura Y, Iga H, Kondo Y, et al. Herpes simplex virus type 1 and type 2 infection in human oral mucosa in culture. *J Oral Pathol Med* 1991; 20: 68-73.
20. Rones Y, Hochman N, Ehrlich J, Zakay-Rones Z. Sensitivity of oral tissues to herpes simplex virus-in vitro. *J Periodontol* 1983; 54: 91-95.
21. Hung S-L, Wang Y-H, Chen H-W, Lee P-L, Chen Y-T. Analysis of herpes simplex virus entering into cells of oral origin. *Virus Res* 2002; 86: 59-69.
22. Furman P A, St Clair M H, Spector T. Acyclovir triphosphate is a suicide inactivator of the herpes simplex virus DNA polymerase. *J Biol Chem* 1984; 259: 9575-9579.
23. Morfin F, Thouvenot D. Herpes simplex virus resistance to antiviral drugs *J Clin Virol* 2003; 26: 29-37.
24. Field H J. Herpes simplex virus antiviral drug resistance—current trends and future prospects. *J Clin Virol* 2001; 21: 261-269.
25. Huang, H. C., et al., Entry of hepatitis B virus into immortalized human primary hepatocytes by clathrin-dependent endocytosis. J Virol. 86(17): p. 9443-53.
26. Lin S C, Liu C J, Chiu C P, Chang S M, Lu S Y, Chen Y J. Establishment of OC3 oral carcinoma cell line and identification of NF-kappa B activation responses to areca nut extract, *J Oral Pathol Med* 2004; 33: 79-86.

What is claimed is:

1. A method for inhibiting hepatitis virus D infection comprising:
    administering to a subject in need thereof a pharmaceutical composition comprising a therapeutically effective amount of an active compound selected from the group consisting of:

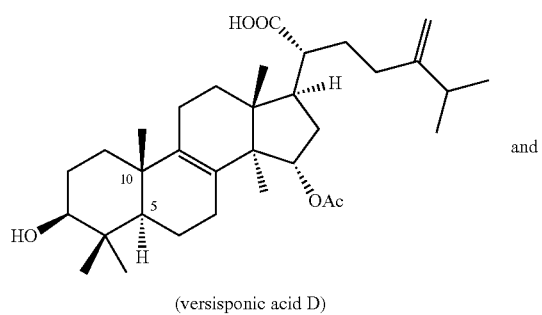

(versisponic acid D)

and

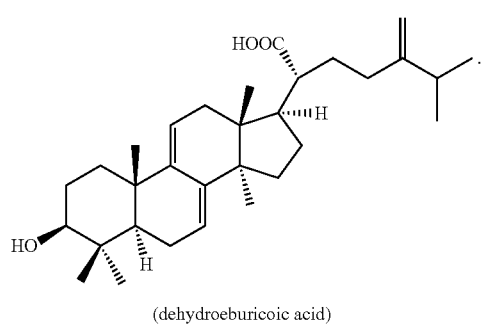

(dehydroeburicoic acid)

2. The method of claim 1, in which the active compound is effective in inhibiting a virus replication, an assembly or a release of viral particles.

3. The method of claim 1, in which the active compound is effective in inhibiting an entry of virus.

4. The method of claim 1, further comprising administering at least one additional therapeutic agent.

5. The method of claim 1, wherein the active compound is

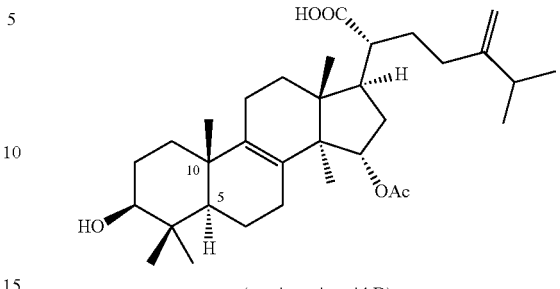

(versisponic acid D)

6. The method of claim 1, wherein the active compound is

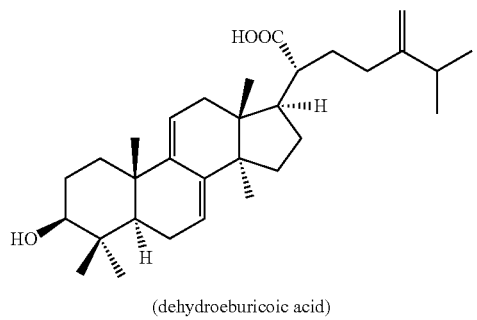

(dehydroeburicoic acid)

* * * * *